US010883996B2

(12) United States Patent
O'Connell et al.

(10) Patent No.: US 10,883,996 B2
(45) Date of Patent: Jan. 5, 2021

(54) METHODS OF IDENTIFYING SIGNALING MODULATORS OF THE TRIMERIC TNFA

(71) Applicant: UCB BIOPHARMA SRL, Brussels (BE)

(72) Inventors: James Philip O'Connell, Slough (GB); John Robert Porter, Slough (GB); Alastair Lawson, Slough (GB); Boris Kroeplien, Slough (GB); Stephen Edward Rapecki, Slough (GB); Timothy John Norman, Slough (GB); David James McMillan, Slough (GB); Graham John Warrellow, Slough (GB); Daniel Christopher Brookings, Slough (GB); Rikki Peter Alexander, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 0 days.

(21) Appl. No.: 15/736,336

(22) PCT Filed: Oct. 22, 2015

(86) PCT No.: PCT/EP2015/074490
§ 371 (c)(1),
(2) Date: Dec. 14, 2017

(87) PCT Pub. No.: WO2016/202411
PCT Pub. Date: Dec. 22, 2016

(65) Prior Publication Data
US 2018/0203016 A1    Jul. 19, 2018

(30) Foreign Application Priority Data

Jun. 18, 2015 (GB) .................. 1510758.4

(51) Int. Cl.
| | |
|---|---|
| *G01N 33/68* | (2006.01) |
| *C07K 14/525* | (2006.01) |
| *C07K 14/705* | (2006.01) |
| *C07K 16/24* | (2006.01) |
| *C07D 401/14* | (2006.01) |
| *C07D 471/00* | (2006.01) |
| *C07D 213/72* | (2006.01) |
| *C07D 235/04* | (2006.01) |
| *C07D 239/26* | (2006.01) |
| *C07D 471/04* | (2006.01) |
| *A61K 47/64* | (2017.01) |
| *A61P 37/00* | (2006.01) |
| *A61P 35/00* | (2006.01) |

(52) U.S. Cl.
CPC ..... *G01N 33/6845* (2013.01); *A61K 47/6425* (2017.08); *A61P 35/00* (2018.01); *A61P 37/00* (2018.01); *C07D 213/72* (2013.01); *C07D 235/04* (2013.01); *C07D 239/26* (2013.01); *C07D 401/14* (2013.01); *C07D 471/00* (2013.01); *C07D 471/04* (2013.01); *C07K 14/525* (2013.01); *C07K 14/70575* (2013.01); *C07K 16/241* (2013.01); *G01N 33/6854* (2013.01); *G01N 33/6863* (2013.01); *C07K 2317/55* (2013.01); *C07K 2317/92* (2013.01); *G01N 2333/525* (2013.01); *G01N 2500/02* (2013.01)

(58) Field of Classification Search
CPC ............ C07K 16/241; C07K 14/70575; C07K 14/525; C07K 2317/92; G01N 2500/02
See application file for complete search history.

(56) References Cited

U.S. PATENT DOCUMENTS

| | | | |
|---|---|---|---|
| 4,908,372 | A | 3/1990 | Carr et al. |
| 7,691,815 | B2 | 4/2010 | Liang |
| 7,993,636 | B2 | 8/2011 | Mayumi et al. |
| 8,377,441 | B2 | 2/2013 | Chang |
| 9,908,944 | B2 | 3/2018 | Padkjaer et al. |
| 10,428,148 | B2 | 10/2019 | Katagiri et al. |
| 10,705,094 | B2 | 7/2020 | O'Connell et al. |
| 10,775,385 | B2 | 9/2020 | O'Connell et al. |
| 2001/0018507 | A1 | 8/2001 | Rathjen et al. |
| 2002/0110868 | A1 | 8/2002 | Dahiyat et al. |
| 2003/0060461 | A1 | 3/2003 | Kodama et al. |
| 2004/0067982 | A1 | 4/2004 | Zheng et al. |
| 2006/0222624 | A1 | 10/2006 | Bratt et al. |
| 2007/0117755 | A1 | 5/2007 | Liang |
| 2009/0022659 | A1 | 1/2009 | Olson et al. |
| 2009/0269357 | A1 | 10/2009 | Ke et al. |
| 2010/0266613 | A1 | 10/2010 | Harding et al. |
| 2010/0297111 | A1 | 11/2010 | Beirnaert |
| 2011/0250130 | A1 | 10/2011 | Benatuil et al. |

(Continued)

FOREIGN PATENT DOCUMENTS

| | | |
|---|---|---|
| CA | 2005053 A1 | 6/1990 |
| CN | 1204230 A | 1/1999 |

(Continued)

OTHER PUBLICATIONS

Alzani et al., Biochemistry 34:6344-6350 (1995).

(Continued)

*Primary Examiner* — Elly-Gerald Stoica

(74) *Attorney, Agent, or Firm* — Medler Ferro Woodhouse & Mills PLLC

(57) ABSTRACT

The invention is in the field of TNF signalling. Compounds have been identified which are capable of modulating signalling of TNF trimers through receptors. Methods of identifying such compounds are therefore provided. The compounds themselves have utility in therapy.

5 Claims, 15 Drawing Sheets
Specification includes a Sequence Listing.

(56) References Cited

U.S. PATENT DOCUMENTS

| | | |
|---|---|---|
| 2013/0018105 A1 | 1/2013 | Carroll et al. |
| 2014/0112929 A1 | 4/2014 | Batuwangala et al. |
| 2014/0165223 A1 | 6/2014 | Ntouni et al. |

FOREIGN PATENT DOCUMENTS

| | | |
|---|---|---|
| CN | 1700930 A | 11/2015 |
| EP | 0288088 A2 | 10/1988 |
| EP | 0492448 A1 | 7/2011 |
| JP | H0596 A | 1/1993 |
| JP | 2003-040888 A | 2/2003 |
| JP | 2008-539772 A | 11/2008 |
| JP | 2010-172307 A | 8/2010 |
| JP | 2011519836 A | 7/2011 |
| JP | 2012-509312 A | 4/2012 |
| WO | WO 93/06489 A1 | 4/1993 |
| WO | WO 93/14083 A1 | 7/1993 |
| WO | 94/18325 A1 | 8/1994 |
| WO | 1997/22587 A1 | 6/1997 |
| WO | WO 02/098869 A2 | 12/2002 |
| WO | 2004/012673 A2 | 2/2004 |
| WO | 2006/122786 A2 | 11/2006 |
| WO | 2007/060411 A1 | 5/2007 |
| WO | 2009/020848 A2 | 8/2008 |
| WO | 2008/144757 A1 | 11/2008 |
| WO | WO 2008/144753 A2 | 11/2008 |
| WO | 2009/132037 A1 | 10/2009 |
| WO | WO 2009/155723 A2 | 12/2009 |
| WO | 2010/058419 A1 | 5/2010 |
| WO | WO 2010/118404 A2 | 10/2010 |
| WO | WO 2012/078878 A2 | 6/2012 |
| WO | WO 2013/024040 A2 | 2/2013 |
| WO | WO 2013/186229 A1 | 12/2013 |
| WO | WO 2014/001557 A1 | 1/2014 |
| WO | WO 2014/009295 A1 | 1/2014 |
| WO | WO 2014/009296 A1 | 1/2014 |
| WO | WO 2014/040076 A1 | 3/2014 |
| WO | WO 2014/123696 A1 | 8/2014 |
| WO | WO 2014/165223 A1 | 10/2014 |
| WO | WO 2015/086496 A1 | 6/2015 |
| WO | WO 2015/086498 A1 | 6/2015 |
| WO | WO 2015/086499 A1 | 6/2015 |
| WO | WO 2015/086500 A1 | 6/2015 |
| WO | WO 2015/086501 A1 | 6/2015 |
| WO | WO 2015/086502 A1 | 6/2015 |
| WO | WO 2015/086503 A1 | 6/2015 |
| WO | WO 2015/086504 A1 | 6/2015 |
| WO | WO 2015/086505 A1 | 6/2015 |
| WO | WO 2015/086506 A1 | 6/2015 |
| WO | WO 2015/086507 A1 | 6/2015 |
| WO | WO 2015/086508 A1 | 6/2015 |
| WO | WO 2015/086509 A1 | 6/2015 |
| WO | WO 2015/086511 A1 | 6/2015 |
| WO | WO 2015/086512 A1 | 6/2015 |
| WO | WO 2015/086513 A1 | 6/2015 |
| WO | WO 2015/086519 A1 | 6/2015 |
| WO | WO 2015/086520 A1 | 6/2015 |
| WO | WO 2015/086521 A1 | 6/2015 |
| WO | WO 2015/086523 A1 | 6/2015 |
| WO | WO 2015/086525 A1 | 6/2015 |
| WO | WO 2015/086526 A1 | 6/2015 |
| WO | WO 2015/086527 A1 | 6/2015 |
| WO | WO 2016/050975 A1 | 4/2016 |
| WO | WO 2016/149436 A1 | 9/2016 |
| WO | WO 2016/149437 A1 | 9/2016 |
| WO | WO 2016/149439 A1 | 9/2016 |
| WO | WO 2016/168633 A1 | 10/2016 |
| WO | WO 2016/168638 A1 | 10/2016 |
| WO | WO 2016/168641 A1 | 10/2016 |
| WO | WO 2016/198398 A1 | 12/2016 |
| WO | WO 2016/198400 A1 | 12/2016 |
| WO | WO 2016/198401 A1 | 12/2016 |
| WO | WO 2016/202412 A1 | 12/2016 |
| WO | WO 2016/202413 A1 | 12/2016 |
| WO | WO 2016/202414 A1 | 12/2016 |
| WO | WO 2016/202415 A1 | 12/2016 |
| WO | WO 2017/023902 A1 | 2/2017 |
| WO | WO 2017/023905 A1 | 2/2017 |
| WO | WO 2017/167993 A1 | 10/2017 |
| WO | WO 2017/167994 A1 | 10/2017 |
| WO | WO 2017/167995 A1 | 10/2017 |
| WO | WO 2017/167996 A1 | 10/2017 |

OTHER PUBLICATIONS

Andersen et al., Protein Science 15:2558-2567 (2006).
Baldwin et al., PNAS 93:1021-1026 (1996).
Eck et al., Journal of Biological Chemistry 264:17595-17605 (1989).
Ganesan et al., Pharmazie 67:374-379 (2012).
Garcia et al. In: D. Wallach et al. (eds), Advances in TNF Family Research, Advances in Experimental Medicine and Biology 691:187-201 (2011), DOI 10.1007/978-1-4419-6612-4_20.
Grell et al., Cell 83:793-802 (1995).
He et al., Science 310:1022-1025 (2005).
Hoffmann et al., PLOS One 7:e31298 (2012).
Hu et al., Journal of Biological Chemistry 288:27059-27067 (2013).
Jones et al., Journal of Cell Science S13:11-18 (1990).
Kim et al., Journal of Molecular Biology 374:1374-1388 (2007).
Liang et al., Journal of Biological Chemistry 288:13799-13807 (2013).
Loetscher et al., Journal of Biological Chemistry 266:18324-18329 (1991).
Ma et al., Journal of Biological Chemistry 289:12457-12466 (2014).
Mascarenhas et al., BMC Structural Biology 12:8 (2012).
Nesbitt et al., Inflammatory Bowel Diseases 13:1323-1332 (2007).
Silvian et al., ACS Chemical Biology 6:636-647 (2011).
Simon et al., Nature Chemical Biology 9:200-205 (2013).
Sudhamsu et al., PNAS 110:19896-19901 (2013).
Tracey et al., Pharmacology & Therapeutics 117:244-279 (2007).
Zalevsky et al., Journal of Immunology 179:1872-1883 (2007).
Zhu et al., Immunology Letters 102:177-183 (2006).
Non-Final Office Action issued in U.S. Appl. No. 15/736,520, dated Feb. 28, 2019.
Non-Final Office Action issued in U.S. Appl. No. 15/736,535, dated Apr. 25, 2019.
Non-Final Office Action issued in U.S. Appl. No. 15/736,558 dated Apr. 26, 2019.
Lloyd et al., "Modelling the human immune response: performance of a $10^{11}$ human antibody repertoire against a broad panel of therapeutically relevant antigens," Protein Engineering, Design & Selection 22(3):159-168 (2009).
Cha et al., "High Resolution Crystal Structure of a Human Tumor Necrosis Factor-α Mutant with Low Systemic Toxicity," The Journal of Biological Chemistry 273(4):2153-2160 (1998).
Mukai et al., "Solution of the Structure of the TNF-TNFR2 Complex," Biochemistry 3(148):1-11 (2010).
Notice of Allowance in U.S. Appl. No. 15/736,614 dated Apr. 6, 2020.
Non-final Office Action in U.S. Appl. No. 15/736,558 dated Apr. 21, 2020.
Fang et al., "TNF: a structure and function relationship," Foreign Medical Immunology, vol. 26, No. 2. (2003). [Machine translation].
Sedger et al., "TNF and TNF-receptors: From Mediators of Cell Death and Inflammation to Therapeutic Giants—Past, Present, and Future," Cytokine & Growth Factor Reviews, 25:453-473 (2014).
Shibata et al., "Creation and X-ray Structure Analysis of the Tumor Necrosis Factor Receptor-1-selective Mutant of a Tumor Necrosis Factor-alpha Antagonist," J. Biol. Chem, 283(2): 998-1007 (2008).
Final Office Action issued in U.S. Appl. No. 15/736,520, dated Oct. 7, 2019.
Final Office Action issued in U.S. Appl. No. 15/736,558, dated Nov. 8, 2019.
Non-Final Office Action issued in U.S. Appl. No. 15/736,614, dated Aug. 29, 2019.
Final Office Action issued in U.S. Appl. No. 15/736,535, dated Nov. 8, 2019.
Notice of Allowance issued in U.S. Appl. No. 15/736,520, dated Feb. 26, 2020.

(56) References Cited

OTHER PUBLICATIONS

Chinese Patent Office Search Report issued in CN Application No. 201580081000.1 dated Aug. 20, 2018.
Non-final Office Action in U.S. Appl. No. 15/736,535 dated May 4, 2020.
Non-final Office Action in U.S. Appl. No. 16/470,999 dated Sep. 10, 2020.
Notice of Allowance dated Sep. 25, 2020 in U.S. Appl. No. 15/736,535.
Final Office Action dated Oct. 8, 2020 in U.S. Appl. No. 15/736,558.

Compound (1)

Compound (2)

Compound (3)

Compound (4)

Compound (5)

Fig. 5
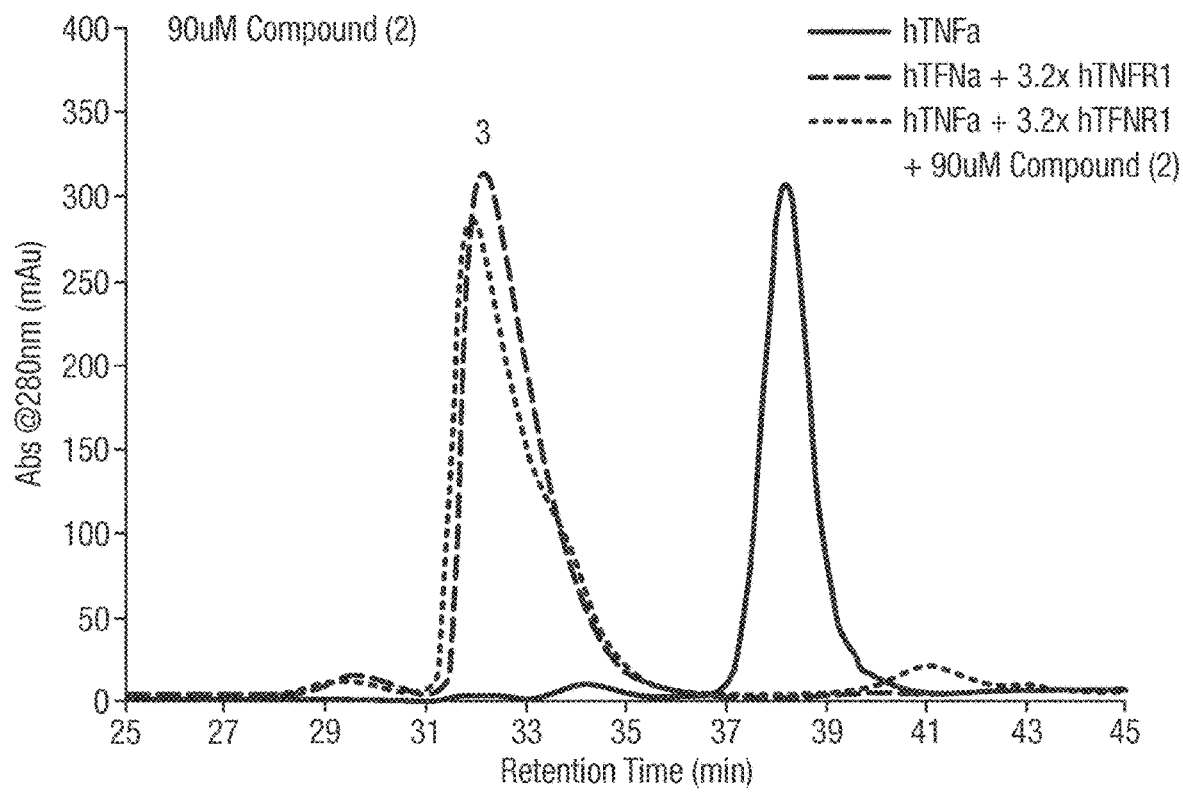
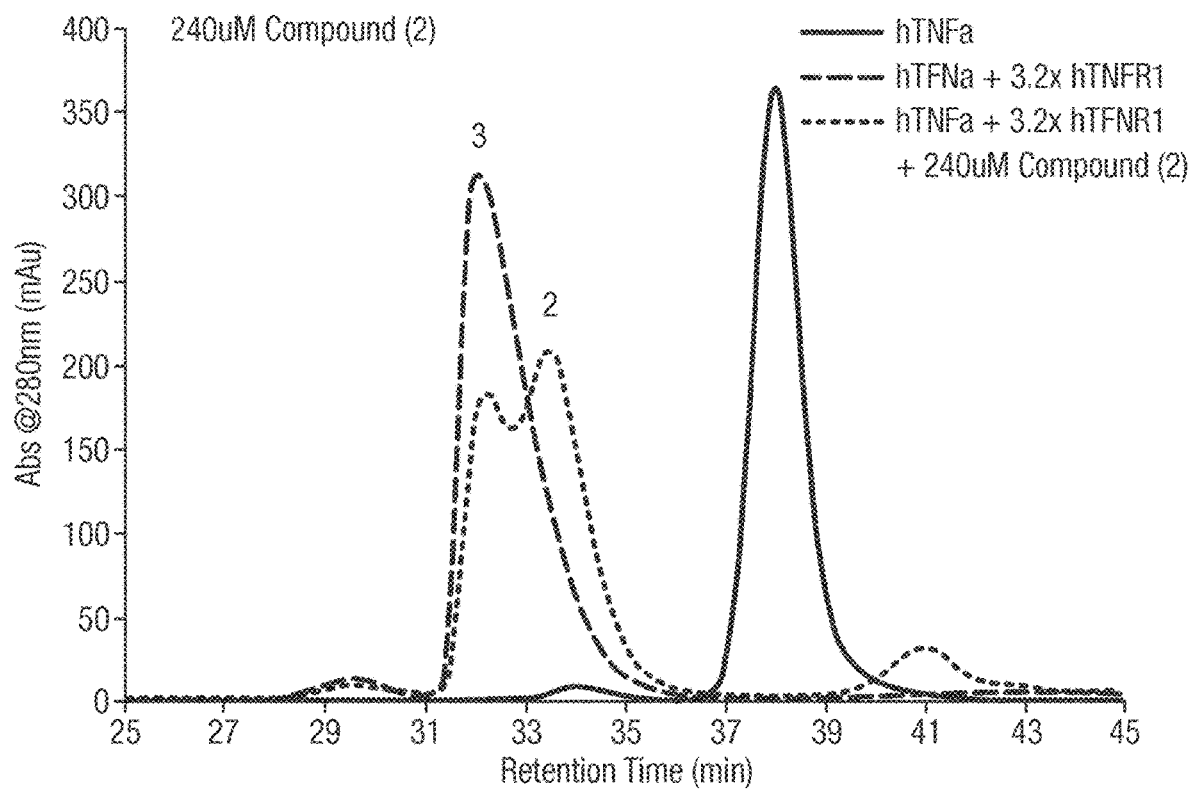

Fig. 5(Cont.)
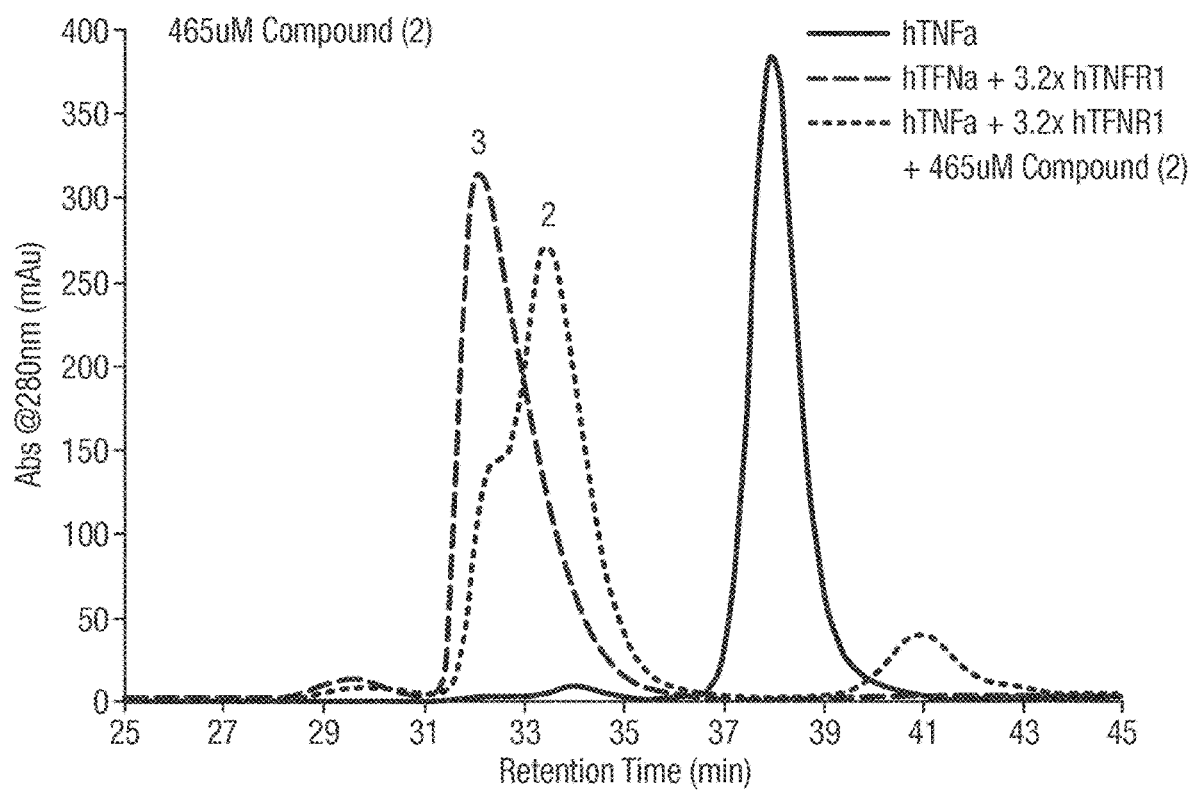
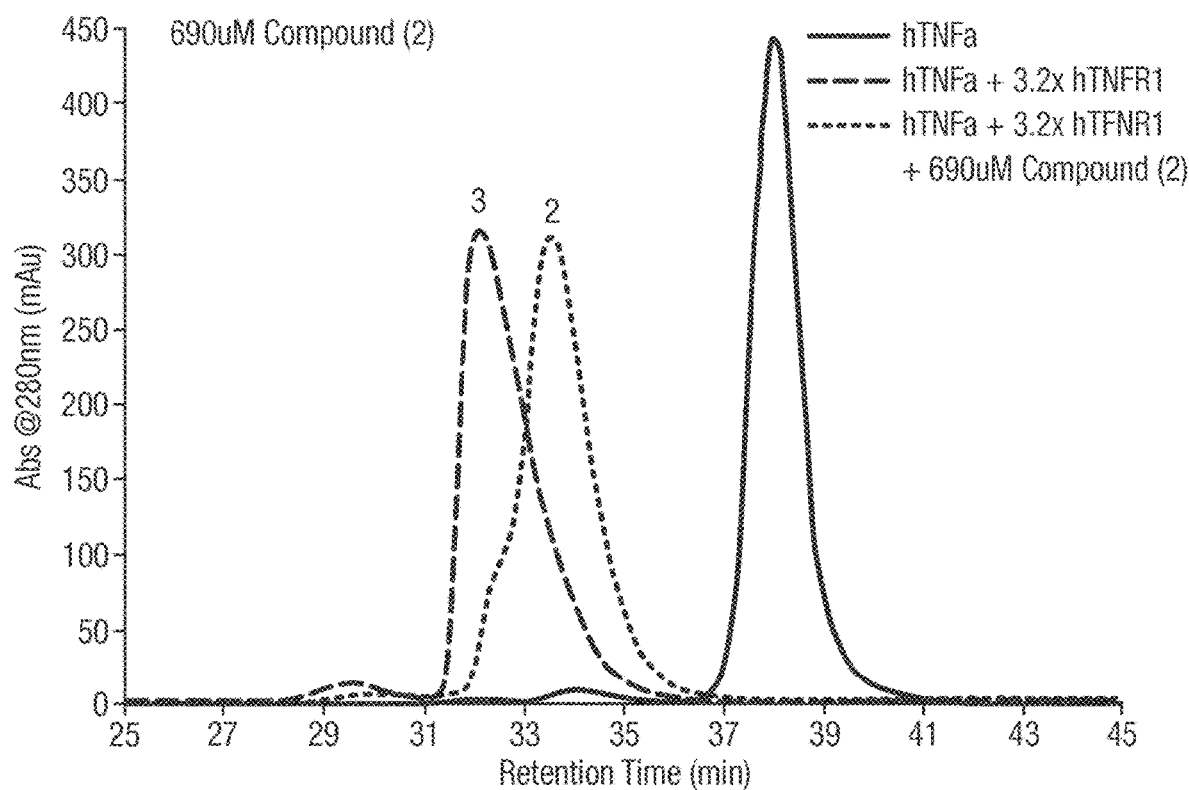

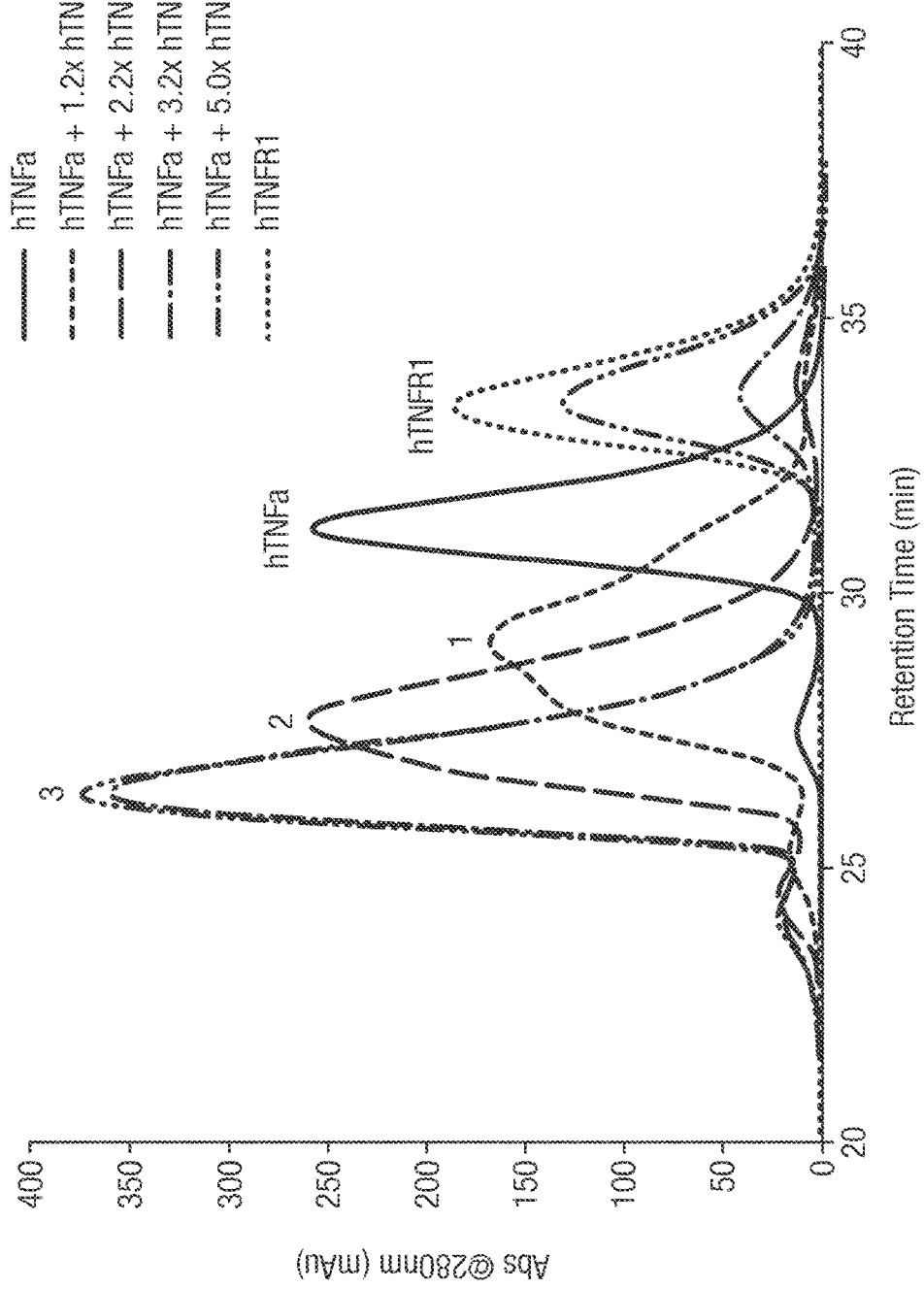

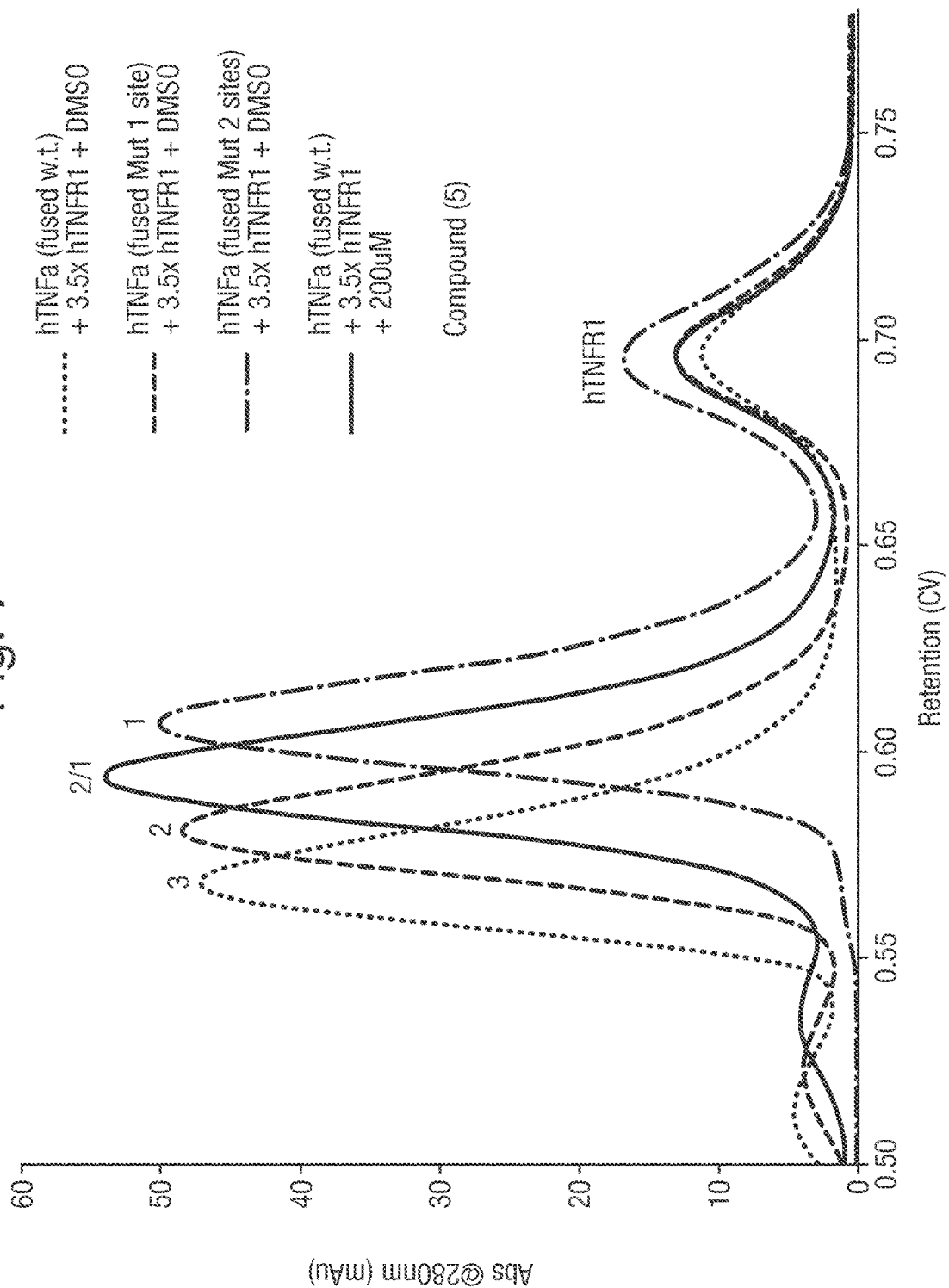

Compound (3)

Compound (4)

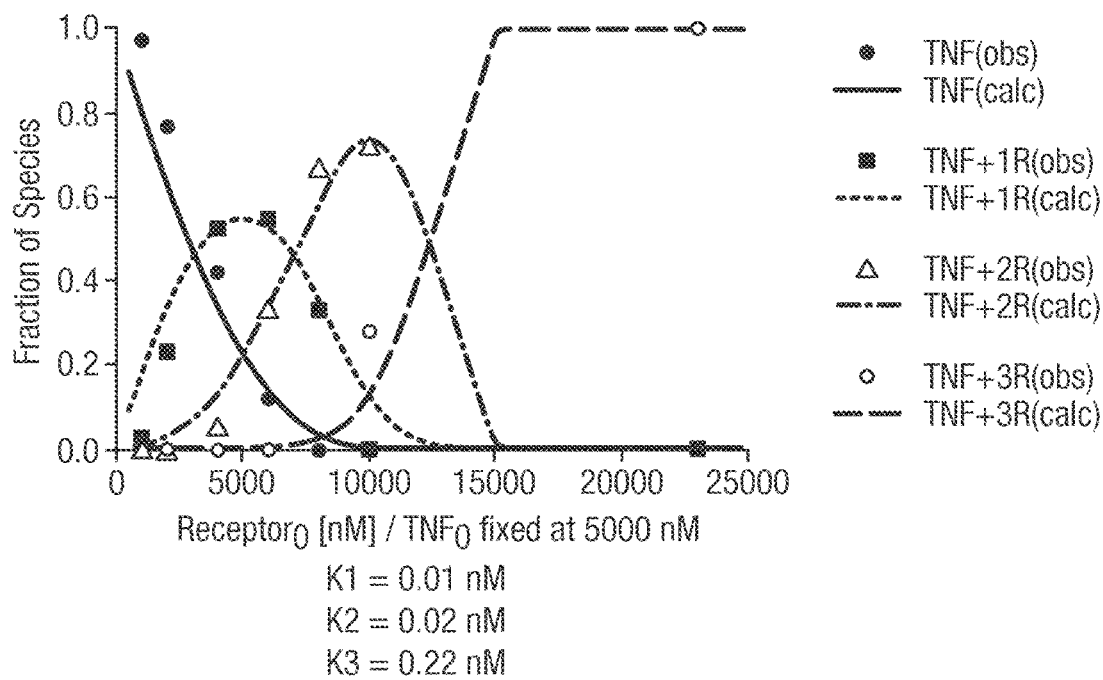
Fig. 12 Human TNF / Human TNFR1 No Compound
K1 = 0.01 nM
K2 = 0.02 nM
K3 = 0.22 nM
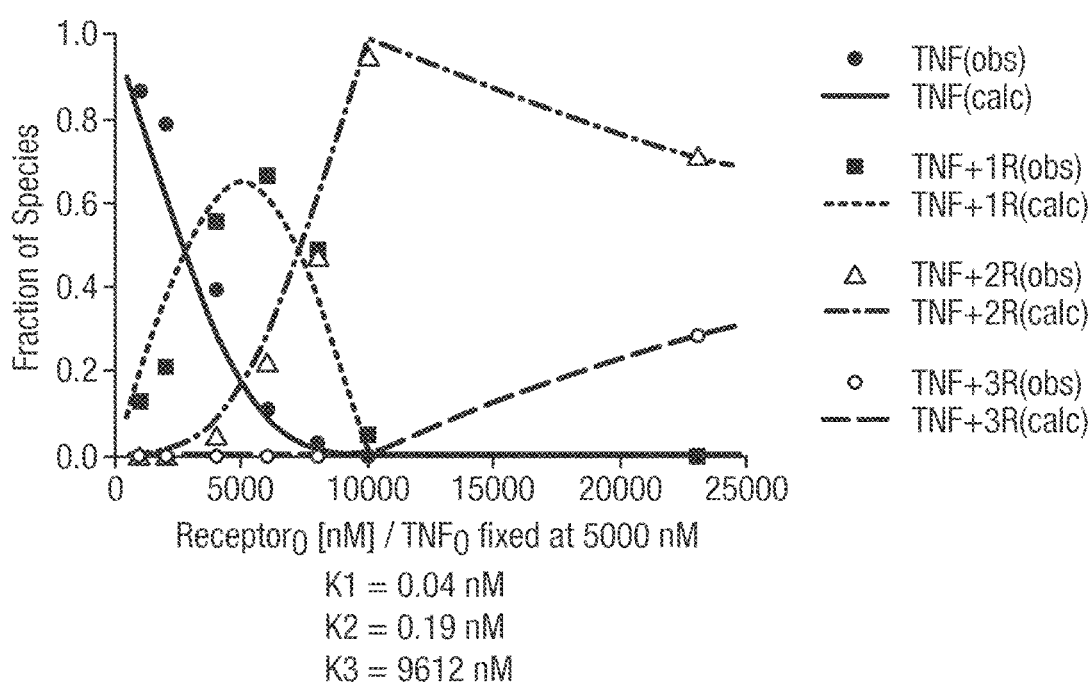
Fig. 13 Human TNF / Human TNFR1 Compound (3)
K1 = 0.04 nM
K2 = 0.19 nM
K3 = 9612 nM

SEQUENCE LISTING

<160> NUMBER OF SEQ ID NOS: 10

<210> SEQ ID NO 1
<211> LENGTH: 147
<212> TYPE: PRT
<213> ORGANISM: Mus musculus

<400> SEQUENCE: 1

Asp Lys Pro Val Ala His Val Val Ala Asn His Gln Val Glu Glu Gln
1               5                   10                  15

Leu Glu Trp Leu Ser Gln Arg Ala Asn Ala Leu Leu Ala Asn Gly Met
            20                  25                  30

Asp Leu Lys Asp Asn Gln Leu Val Val Pro Ala Asp Gly Leu Tyr Leu
        35                  40                  45

Val Tyr Ser Gln Val Leu Phe Lys Gly Gln Gly Cys Pro Asp Tyr Val
    50                  55                  60

Leu Leu Thr His Thr Val Ser Arg Phe Ala Ile Ser Tyr Gln Glu Lys
65                  70                  75                  80

Val Asn Leu Leu Ser Ala Val Lys Ser Pro Cys Pro Lys Asp Thr Pro
                85                  90                  95

Glu Gly Ala Glu Leu Lys Pro Trp Tyr Glu Pro Ile Tyr Leu Gly Gly
            100                 105                 110

Val Phe Gln Leu Glu Lys Gly Asp Gln Leu Ser Ala Glu Val Asn Leu
        115                 120                 125

Pro Lys Tyr Leu Asp Phe Ala Glu Ser Gly Val Tyr Phe Gly Val
    130                 135                 140

Ile Ala Leu
145

<210> SEQ ID NO 2
<211> LENGTH: 144
<212> TYPE: PRT
<213> ORGANISM: Homo sapiens

<400> SEQUENCE: 2

Gly Ser Val Cys Pro Gln Gly Lys Tyr Ile His Pro Gln Asp Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Ser Ser Asn
    130                 135                 140

<210> SEQ ID NO 3
<211> LENGTH: 121
<212> TYPE: PRT

```
<213> ORGANISM: Artificial Sequence
<220> FEATURE:
<223> OTHER INFORMATION: HCVR of 1974

<400> SEQUENCE: 3

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
            20                  25                  30

Tyr Met Ala Trp Val Arg Gln Ala Pro Thr Lys Gly Leu Glu Trp Val
        35                  40                  45

Ala Ser Ile Asn Tyr Asp Gly Ala Asn Thr Phe Tyr Arg Asp Ser Val
    50                  55                  60

Lys Gly Arg Phe Thr Val Ser Arg Asp Asn Ala Arg Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: LCVR of 1974

<400> SEQUENCE: 4

Asp Ile Gln Met Thr Gln Ser Pro Ala Ser Leu Pro Ala Ser Pro Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Ala
    50                  55                  60

Ser Arg Ser Gly Thr Gln Tyr Ser Leu Lys Ile Ser Arg Leu Gln Val
65                  70                  75                  80

Glu Asp Phe Gly Ile Phe Tyr Cys Leu Gln Gly Gln Ser Thr Pro Tyr
                85                  90                  95

Thr Phe Gly Ala Gly Thr Lys Leu Glu Leu Lys
            100                 105

<210> SEQ ID NO 5
<211> LENGTH: 445
<212> TYPE: PRT
<213> ORGANISM: Artificial Sequence
<220> FEATURE:
<223> OTHER INFORMATION: 1974 HC mIgG1 full

<400> SEQUENCE: 5

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
            20                  25                  30

Tyr Met Ala Trp Val Arg Gln Ala Pro Thr Lys Gly Leu Glu Trp Val
        35                  40                  45
```

Ala Ser Ile Asn Tyr Asp Gly Ala Asn Thr Phe Tyr Arg Asp Ser Val
         50                  55                  60

Lys Gly Arg Phe Thr Val Ser Arg Asp Asn Ala Arg Ser Ser Leu Tyr
 65                  70                  75                  80

Leu Gln Met Asp Ser Leu Arg Ser Glu Asp Thr Ala Thr Tyr Tyr Cys
                     85                  90                  95

Thr Thr Glu Ala Tyr Gly Tyr Asn Ser Asn Trp Phe Gly Tyr Trp Gly
                100                 105                 110

Gln Gly Thr Leu Val Thr Val Ser Ser Ala Lys Thr Thr Pro Pro Ser
            115                 120                 125

Val Tyr Pro Leu Ala Pro Gly Ser Ala Ala Gln Thr Asn Ser Met Val
130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
                180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
                260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
                340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
                420                 425                 430

His His Thr Glu Lys Ser Leu Ser His Ser Pro Gly Lys
            435                 440                 445

<210> SEQ ID NO 6
<211> LENGTH: 214

<212> TYPE: PRT
<213> ORGANISM: Artificial Sequence
<220> FEATURE:
<223> OTHER INFORMATION: 1974 LC kappa full

<400> SEQUENCE: 6

Asp Ile Gln Met Thr Gln Ser Pro Ala Ser Leu Pro Ala Ser Pro Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Ala
    50                  55                  60

Ser Arg Ser Gly Thr Gln Tyr Ser Leu Lys Ile Ser Arg Leu Gln Val
65                  70                  75                  80

Glu Asp Phe Gly Ile Phe Tyr Cys Leu Gln Gly Gln Ser Thr Pro Tyr
                85                  90                  95

Thr Phe Gly Ala Gly Thr Lys Leu Glu Leu Lys Arg Thr Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 7
<211> LENGTH: 120
<212> TYPE: PRT
<213> ORGANISM: Artificial Sequence
<220> FEATURE:
<223> OTHER INFORMATION: HCVR of 1979

<400> SEQUENCE: 7

Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
            20                  25                  30

Tyr Trp Asp Trp Ile Arg Lys Phe Pro Gly Asn Lys Met Glu Trp Met
        35                  40                  45

Gly Tyr Ile Asn Tyr Ser Gly Ser Thr Gly Tyr Asn Pro Ser Leu Lys
    50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
            100                 105                 110

Gly Val Met Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: LCVR of 1979

<400> SEQUENCE: 8

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro His Leu Leu Ile
        35                  40                  45

Tyr Gly Thr Thr Ser Leu Ala Asp Gly Val Pro Ser Arg Phe Ser Gly
    50                  55                  60

Ser Arg Ser Gly Thr Gln Tyr Ser Leu Lys Ile Ser Gly Leu Gln Val
65                  70                  75                  80

Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys
            100                 105

<210> SEQ ID NO 9
<211> LENGTH: 444
<212> TYPE: PRT
<213> ORGANISM: Artificial Sequence
<220> FEATURE:
<223> OTHER INFORMATION: 1979 HC mIgG1 full

<400> SEQUENCE: 9

Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
            20                  25                  30

Tyr Trp Asp Trp Ile Arg Lys Phe Pro Gly Asn Lys Met Glu Trp Met
        35                  40                  45

Gly Tyr Ile Asn Tyr Ser Gly Ser Thr Gly Tyr Asn Pro Ser Leu Lys
    50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
            100                 105                 110

Gly Val Met Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser

-continued

```
                180                 185                 190
Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 10
<211> LENGTH: 214
<212> TYPE: PRT
<213> ORGANISM: Artificial Sequence
<220> FEATURE:
<223> OTHER INFORMATION: 1979 LC Kappa full

<400> SEQUENCE: 10

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro His Leu Leu Ile
        35                  40                  45

Tyr Gly Thr Thr Ser Leu Ala Asp Gly Val Pro Ser Arg Phe Ser Gly
    50                  55                  60

Ser Arg Ser Gly Thr Gln Tyr Ser Leu Lys Ile Ser Gly Leu Gln Val
65                  70                  75                  80

Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys Arg Thr Asp Ala Ala
```

-continued

```
                100                   105                   110
Pro Thr Val Ser Ile Phe Pro Pro Ser Ser Glu Gln Leu Thr Ser Gly
        115                   120                   125

Gly Ala Ser Val Val Cys Phe Leu Asn Asn Phe Tyr Pro Lys Asp Ile
        130                   135                   140

Asn Val Lys Trp Lys Ile Asp Gly Ser Glu Arg Gln Asn Gly Val Leu
145                   150                   155                   160

Asn Ser Trp Thr Asp Gln Asp Ser Lys Asp Ser Thr Tyr Ser Met Ser
                165                   170                   175

Ser Thr Leu Thr Leu Thr Lys Asp Glu Tyr Glu Arg His Asn Ser Tyr
                180                   185                   190

Thr Cys Glu Ala Thr His Lys Thr Ser Thr Ser Pro Ile Val Lys Ser
        195                   200                   205

Phe Asn Arg Asn Glu Cys
        210
```

METHODS OF IDENTIFYING SIGNALING MODULATORS OF THE TRIMERIC TNFA

REFERENCE TO AN ELECTRONIC SEQUENCE LISTING

The contents of the electronic sequence listing (00890003US1seqlist.txt; Size: 18,963 bytes; and Date of Creation Dec. 13, 2017) is herein incorporated by reference in its entirety.

FIELD OF THE INVENTION

The present invention relates to methods for identifying compounds which modulate signalling of TNF superfamily member trimers through TNF receptors. In particular, the invention relates to identification of new small molecule modulators. The invention also relates to compounds identified by such methods and complexes of the compounds and trimers. The compounds and complexes may be used therapeutically.

BACKGROUND OF THE INVENTION

The Tumour Necrosis Factor (TNF) superfamily is a family of proteins that share a primary function of regulating cell survival and cell death. Members of the TNF superfamily share a common core motif, which consists of two antiparallel β-pleated sheets with antiparallel β-strands, forming a "jelly roll" β-structure. Another common feature shared by members of the TNF superfamily is the formation of homo- or heterotrimeric complexes. It is these trimeric forms of the TNF superfamily members that bind to, and activate, specific TNF superfamily receptors.

TNFα is the archetypal member of the TNF superfamily. Dysregulation of TNFα production has been implicated in a number of pathological conditions of significant medical importance. For example, TNFα has been implicated in rheumatoid arthritis, inflammatory bowel diseases (including Crohn's disease), psoriasis, Alzheimer's disease (AD), Parkinson's disease (PD), pain, epilepsy, osteoporosis, asthma, systemic lupus erythematosus (SLE) and multiple sclerosis (MS). Other members of the TNF superfamily have also been implicated in pathological conditions, including autoimmune disease.

Conventional antagonists of TNF superfamily members are macromolecular and act by inhibiting the binding of the TNF superfamily member to its receptor. Examples of conventional antagonists include anti-TNFα antibodies, particularly monoclonal antibodies, such as infliximab (Remicade®), adalimumab (Humira®) and certolizumab pegol (Cimzia®), or soluble TNFα receptor fusion proteins, such as etanercept (Enbrel®).

SUMMARY OF THE INVENTION

When receptors are present at an equivalent or excess concentration compared with TNF monomers (i.e. at a molar (concentration) ratio of at least 1:1 (receptors:monomers); at least 3:1 (receptors:trimers)), a TNF trimer will typically bind three receptors. The present inventors have identified small molecular entities (SMEs) that modulate TNF signalling. These SME compounds act by binding to the trimeric form of TNF, and inducing and/or stabilising a conformational change in the trimer. Trimers with the compounds bound have an altered affinity for the requisite receptors, especially a reduced affinity for the second and third receptors, which decreases the number of receptors binding per trimer-compound complex. Accordingly, downstream signalling through the receptors is reduced. These compounds can therefore be used in the treatment of conditions mediated by TNF. The present inventors have also developed methods that can identify compounds which are capable of modulating TNF signalling in this manner.

The present invention therefore provides a method of identifying a compound that is capable of binding to a trimeric protein that is a TNF superfamily member and modulating signalling of the trimeric protein through the requisite TNF superfamily receptor, the method comprising determining the average number of receptors bound per trimer-compound complex and thereby identifying whether the compound is capable of modulating signalling through the receptor.

The invention also provides:
- a compound that is capable of binding to a trimeric protein that is a TNF superfamily member and modulating signalling of the TNF superfamily member through the requisite receptor, wherein the compound results in an equivalent average number of receptors bound per trimer-compound complex, or a change in the average number of receptors bound per trimer-compound complex, in comparison with a control;
- a compound of formula (5), or a pharmaceutically acceptable salt or solvate thereof;
- a complex comprising a trimeric protein that is a TNF superfamily member and a compound as defined above;
- a compound or complex as defined above for use in a method of therapy of the human or animal body; and
- a pharmaceutical composition comprising the compound or complex as defined above and a pharmaceutically acceptable carrier.

BRIEF DESCRIPTION OF THE FIGURES

FIG. 4 shows structures of compounds which are capable of modulating signalling of TNF superfamily member trimers through TNF receptors.

FIG. 5 shows results of size exclusion chromatography (SEC) experiments using compound (2), TNFα and TNFR1 (in a 3.2 fold excess relative to the trimer-compound complex). At low concentrations of the compound (90 μM) the predominant peak corresponds to three receptors binding per trimer-compound complex. This peak has a slight shoulder, indicating that some trimer-compound complexes bind two receptors. When the concentration of the compound is increased and is present in an excess (690 μM) relative to the concentration of the TNF trimers, the predominant peak corresponds to two receptors binding per trimer-compound complex. The slight shoulder on the peak does though indicate that some trimers still bind all three receptors. In the Figure, results for controls comprising TNFα alone, and TNFα and TNFR1 (negative controls in the absence of compound), are also presented. In the TNFα and TNFR1 negative controls, three receptors bind per trimer-compound complex. This is achieved by preincubating a 3.2 excess of TNFR1 over TNFα trimer. More data is presented in FIG. 6.

FIG. 6 shows the control for the SEC experiments described in FIG. 5. TNFα was incubated with varying concentrations of TNFR1 (ranging from a 1.2-5 fold excess of receptors:trimers). As an increasing concentration of TNFR1 is added the molecular weight of the complex with TNFα increases (shifts to the left). Addition of a 5 fold excess of TNFR1 over the concentration of TNFα trimers does not increase the molecular weight of the complex over that using a 3.2 fold excess. This suggests that TNFα is saturated at a molar ratio of 3 TNFR1s to 3 TNFα monomers (3 TNFR1s per trimer).

FIG. 7 shows results of SEC experiments using compound (5), TNFα and TNFR1 (in a 3.5 fold excess relative to the concentration of the trimer-compound complex). Results are also presented for controls, the first of which is TNFα and receptors in the absence of compound. The second and third controls are still TNFα and receptors in the absence of compound, but the TNFα is mutated to disrupt interactions at the third, and third and second, receptor binding sites. The control which is TNFα and receptors shows a peak indicating three receptors binding per trimer. The control with a mutation at one receptor binding site shows a peak corresponding to two receptors binding per trimer, and the control with mutations at two sites shows a peak corresponding to one receptor binding per trimer. The peak obtained in the presence of compound (5) is mid-way between the second and third controls, and therefore indicates trimers binding a mixture of two receptors and one receptor respectively.

FIG. 12 shows determination of dissociation constants in a control sample with TNFα and TNFR1. As increasing concentrations of TNFR1 are added to TNFα different mass species appear and then disappear corresponding to the appearance of firstly 1 TNFR1 bound to TNFα, followed by 2 TNFR1 bound to TNFα, and finally 3 TNFR1 bound to TNFα.

FIG. 13 shows determination of dissociation constants in a sample with TNFα, TNFR1 and compound (3). This shows a significantly worse (lower affinity) TNFR1 interaction with TNFα of the third receptor (0.22 nM to 9.612 nM).

Figure 1:
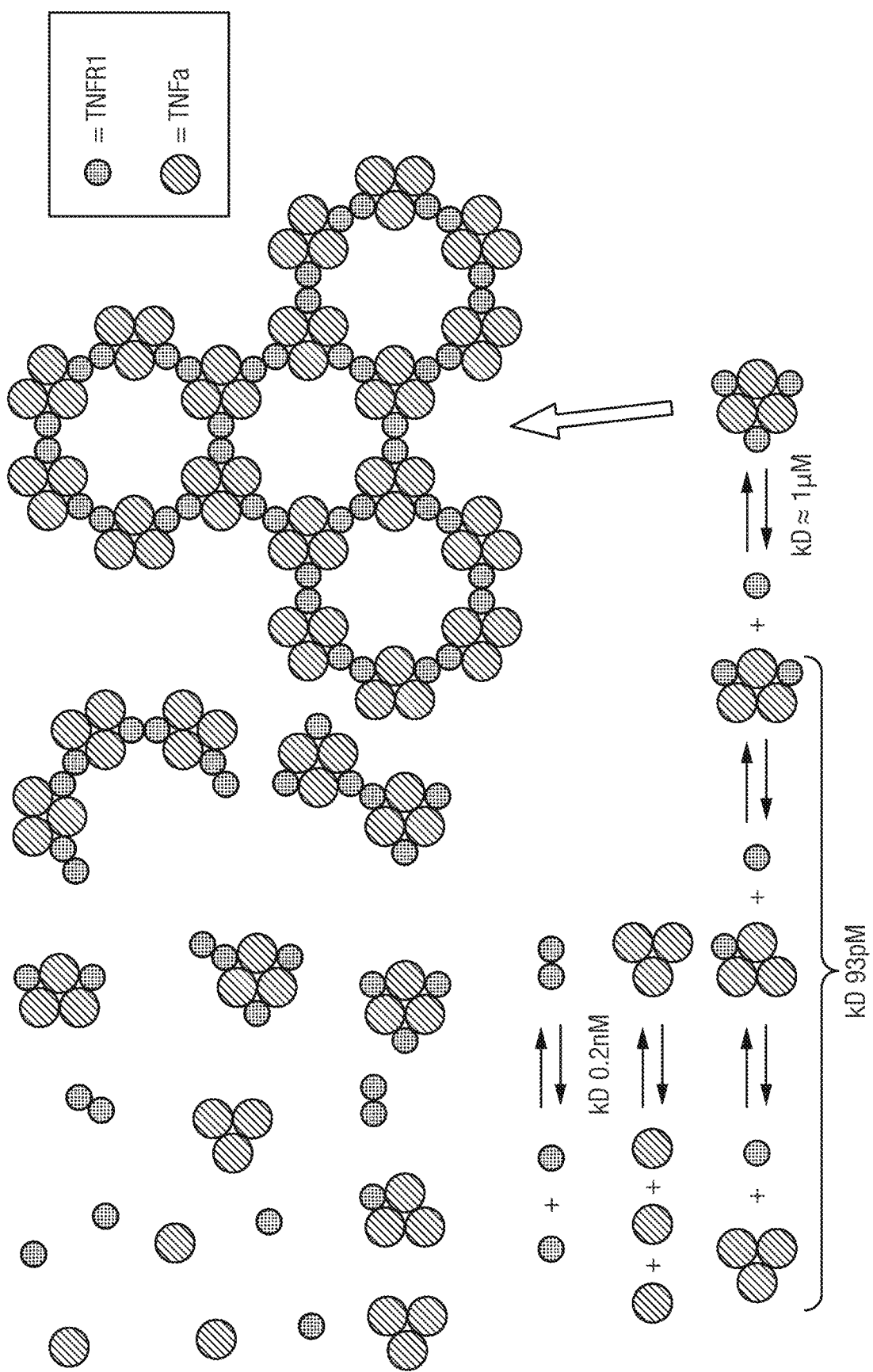
FIG. 1 shows the interactions involved in TNFα/TNF-R1 signalling in the absence of compound. The TNFα trimers bind the first two receptors with a $K_D$ of 93 pM, and bind the third receptor with a $K_D$ of approximately 1 μM. These trimer and receptor complexes (with three receptors bound) then form raft structures via dimerisation of the receptors, which result in downstream signalling.

DESCRIPTION OF THE SEQUENCE LISTING

SEQ ID NOs: 1 and 2 show sequences used in the Examples.

SEQ ID NO: 3 shows the HCVR of C185_01974.0.

SEQ ID NO: 4 shows the LCVR of C185_01974.0.

SEQ ID NO: 5 shows the amino acid sequence of the mIgG1 heavy chain of C185_01974.0.

SEQ ID NO: 6 shows the amino acid sequence of the kappa light chain of C185_01974.0.

SEQ ID NO: 7 shows the HCVR of C185_01979.0.

SEQ ID NO: 8 shows the LCVR of C185_01979.0.

SEQ ID NO: 9 shows the amino acid sequence of the mIgG1 heavy chain of C185_01979.0.

SEQ ID NO: 10 shows the amino acid sequence of the kappa light chain of C185_01979.0.

DETAILED DESCRIPTION OF THE INVENTION

It is to be understood that different applications of the disclosed methods and products may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise.

All publications, patents and patent applications cited herein, whether supra or infra, are hereby incorporated by reference in their entirety.

Methods for Identifying Modulators of TNF Superfamily Members

The present invention relates to methods of (assays for) identifying compounds that are capable of binding to a trimeric protein that is a TNF superfamily member and modulating signalling of the trimeric protein through the requisite TNF superfamily receptor. Compounds identified by the methods of the invention are therefore also known as modulators.

As described further below, the compounds identified by the methods of the invention generally prevent or decrease (inhibit) signalling of TNF through the requisite receptors. Such compounds are antagonists of TNF signalling. However, the methods of the invention may also be used to identify agonist compounds, which increase (enhance) signalling of TNF through the requisite receptors. In both cases, the compounds are capable of modulating TNF signalling without having to compete with the high affinity interaction between the TNF superfamily member and its receptor.

The compounds identified by the methods of the invention bind to the trimeric forms of TNF superfamily members. The compounds are therefore allosteric modulators that bind to the natural agonists of the TNF superfamily receptors, i.e. to trimeric forms of TNF superfamily members. Methods of screening for compounds which are capable of binding to TNF trimers are discussed further below.

There are 22 TNF superfamily members currently known, which are TNFα (TNFSF1A), TNFβ (TNFSF1B), CD40L (TNFSF5), BAFF (TNFSF13B/BlyS), APRIL (TNFSF13), OX40L (TNFSF4), RANKL (TNFSF11/TRANCE), TWEAK (TNFSF12), TRAIL (TNFSF10), TL1A (TNFSF15), LIGHT (TNFSF14), Lymphotoxin, Lymphotoxin β (TNFSF3), 4-1BBL (TNFSF9), CD27L (TNFSF7), CD30L (TNFSF8), EDA (Ectodysplasin), EDA-A1 (Ectodysplasin A1), EDA-A2 (Ectodysplasin A2), FASL (TNFSF6), NGF and GITRL (TNFSF18).

The methods of the invention may be used to identify compounds which modulate signalling of any TNF superfamily member, including the 22 known TNF superfamily members. The compounds identified using the methods of the invention may bind specifically to the trimeric forms of one or more TNF superfamily members. Compounds identified by the methods of the invention may bind specifically to only one of the TNF superfamily members, but not to any other TNF superfamily members. Compounds identified by the methods of the invention may also bind specifically to two, three, four or up to all of the TNF superfamily members.

By specific, it will be understood that the compounds bind to the molecule or molecules of interest, in this case the trimeric form of the TNF superfamily member, with no significant cross-reactivity to any other molecule, which may include other members of the TNF superfamily. Cross-reactivity may be assessed by any suitable method, for example surface plasmon resonance. Cross-reactivity of a compound for the trimeric form of a TNF superfamily member with a molecule other than the trimeric form of that particular TNF superfamily member may be considered significant if the compound binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to the trimeric form of the TNF superfamily member of interest. A compound that is specific for the trimeric form of a TNF superfamily member may bind to another molecule at less than 90%, 85%, 80%, 75%, 70%, 65%, 60%, 55%, 50%, 45%, 40%, 35%, 30%, 25% or 20% the strength that it binds to the trimeric form of the TNF superfamily member. Preferably, the compound binds to the other molecule at less than 20%, less than 15%, less than 10% or less than 5%, less than 2% or less than 1% the strength that it binds to the trimeric form of the TNF superfamily member Preferably, the TNF superfamily member is TNFα. TNFα exists in both a soluble (TNFα$_s$) and membrane-bound form (TNFα$_m$). When TNFα is referred to herein this encompasses both the TNFα$_s$ and TNFα$_m$ forms. Particularly preferably, TNFα is in the TNFα$_s$ form.

There are currently 34 known TNF receptors, which are 4-1BB (TNFRSF9/CD137), NGF R (TNFRSF16), BAFF R (TNFRSF13C), Osteoprotegerin (TNFRSF11B), BCMA (TNFRSF17), OX40 (TNFRSF4), CD27 (TNFRSF7), RANK (TNFRSF11A), CD30 (TNFRSF8), RELT (TNFRSF19L), CD40 (TNFRSF5), TACI (TNFRSF13B), DcR3 (TNFRSF6B), TNFRH3 (TNFRSF26), DcTRAIL R1 (TNFRSF23), DcTRAIL R2 (TNFRSF22), TNF-R1 (TNFRSF1A), TNF-R2 (TNFRSF1B), DR3 (TNFRSF25), TRAIL R1 (TNFRSF10A), DR6 (TNFRSF21), TRAIL R2 (TNFRSF10B), EDAR, TRAIL R3 (TNFRSF10C), Fas (TNFRSF6/CD95), TRAIL R4 (TNFRSF10D), GITR (TNFRSF18), TROY (TNFRSF19), HVEM (TNFRSF 14), TWEAK R (TNFRSF 12A), TRAMP (TNFRSF25), Lymphotoxin β R (TNFRSF3) and XEDAR.

A requisite receptor is a receptor which acts in conjunction with a particular TNF superfamily member. In particular, a requisite receptor is a receptor which is activated by a TNF superfamily member. The TNF superfamily member trimers bind to the receptor and activation of the receptor results in downstream signalling. Combinations of TNF superfamily members and their requisite receptors are known in the art.

Preferably, the methods of the invention are used to identify compounds which modulate signalling through TNF-R1 (TNFR1) and TNF-R2 (TNFR2). When TNF-R is referred to herein this encompasses both TNF-R1 and TNF-R2, including the extracellular domain (ECD) of TNF-R1 and TNF-R2. More preferably, the TNF superfamily member is TNFα and the TNF receptor is TNF-R1 or TNF-R2. Even more preferably, the TNF superfamily member is TNFα and the TNF receptor is TNF-R1. Most preferably, the TNF superfamily member is TNFα$_s$ and the TNF receptor is TNF-R1.

The methods of the invention may be used to identify compounds which act by specifically modulating the signalling of TNF superfamily members through TNF-R1. In particular, the compounds may act by modulating the signalling of TNF superfamily members through TNF-R1, but have no effect on signalling of TNF superfamily members through TNF-R2.

The TNF superfamily members and their receptors may be purified or present in mixtures, such as in cultured cells, tissue samples, body fluids or culture medium.

In the methods of the invention, compounds are identified which modulate signalling of the trimeric protein through the requisite receptors. Modulation of signalling may refer to an increase (enhancement) in signalling through the requisite receptors. Compounds which increase signalling are agonist compounds. However, compounds identified using the methods of the invention generally prevent or decrease (inhibit) signalling through the requisite receptors. Such compounds are known as antagonists.

To detect the level of signalling, assays that measure the downstream effects of TNF superfamily receptor signalling can be performed. For example, a L929 murine fibrosarcoma cell-killing assay can be used to assess the stimulation of cell death by TNF. Inhibition of TNF-induced IL-8 production by human monocytes may also be used to assess whether a test compound inhibits TNF signalling via its receptor. Such assays are well known in the art.

The compounds identified by the methods of the invention may completely or partially inhibit signalling through a TNF receptor when a TNF superfamily member in the form of a compound-trimer complex binds to the receptor. The compound may act to reduce signalling through a TNF superfamily receptor by at least 10%, 20%, 30%, 40%, 50%, 60%, 70%, 80%, 90% or 100%. Any change in the level of signalling may be measured by an appropriate technique, including measuring reporter gene activity by alkaline phosphatase or luciferase, NF-κB translocation using machines such as the Cellomics Arrayscan, phosphorylation of downstream effectors, recruitment of signalling molecules, or cell death.

The compounds identified by the methods of the invention may modulate at least one of the downstream effects of signalling through a TNF receptor when a TNF superfamily member in the form of a compound-trimer complex binds to the receptor. Such effects are discussed herein and include TNF superfamily-induced IL-8, IL17A/F, IL2 and VCAM production, TNF superfamily-induced NF-κB activation and neutrophil recruitment. Standard techniques are known in the art for measuring the downstream effects of TNF superfamily members. The compounds identified by the methods of the invention may modulate at least 1, 2, 3, 4, 5, 10 or up to all of the downstream effects of signalling through a TNF receptor.

The activity of the compounds identified by the methods of the invention may be quantified using standard terminology, such as $IC_{50}$ or half maximal effective concentration ($EC_{50}$) values. $IC_{50}$ values represent the concentration of a compound that is required for 50% inhibition of a specified biological or biochemical function. $EC_{50}$ values represent the concentration of a compound that is required for 50% of its maximal effect. The compounds identified by the methods of the invention may have $IC_{50}$ or $EC_{50}$ values of 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 100 pM or less. $IC_{50}$ and $EC_{50}$ values may be measured using any appropriate technique, for example cytokine production can be quantified using ELISA. $IC_{50}$ and $EC_{50}$ values can then be generated using a standard 4-parameter logistic model also known as the sigmoidal dose response model.

In the present invention, libraries of compounds may be screened in order to identify modulators of TNF superfamily members (i.e. using the methods disclosed herein). Such libraries typically comprise at least 260 compounds. Preferably, such libraries comprise at least 300, at least 500 or even at least 1000 compounds.

In the methods of the invention, the average number of receptors bound per trimer-compound complex is determined in order to identify compounds capable of modulating TNF signalling. In the absence of any compound, when receptors are present at an equivalent or excess concentration compared with TNF monomers (at a molar ratio of greater than 1:1 (receptors:monomers); greater than 3:1 (receptors:trimers)) typically three receptors bind per TNF trimer. These trimer and receptor complexes then form rafts via the formation of receptor dimers. The rafts are responsible for downstream signalling.

This is illustrated in FIG. 1 which shows TNF trimer and receptor interactions, and the formation of rafts, involved in TNFα and TNF-R1 signalling. As shown in the Figure, the TNFα trimers bind the first and second requisite receptors with an affinity ($K_D$) of approximately 93 pM. The trimers then bind the third and final receptor with a $K_D$ of approximately 1 µM.

Figure 2:
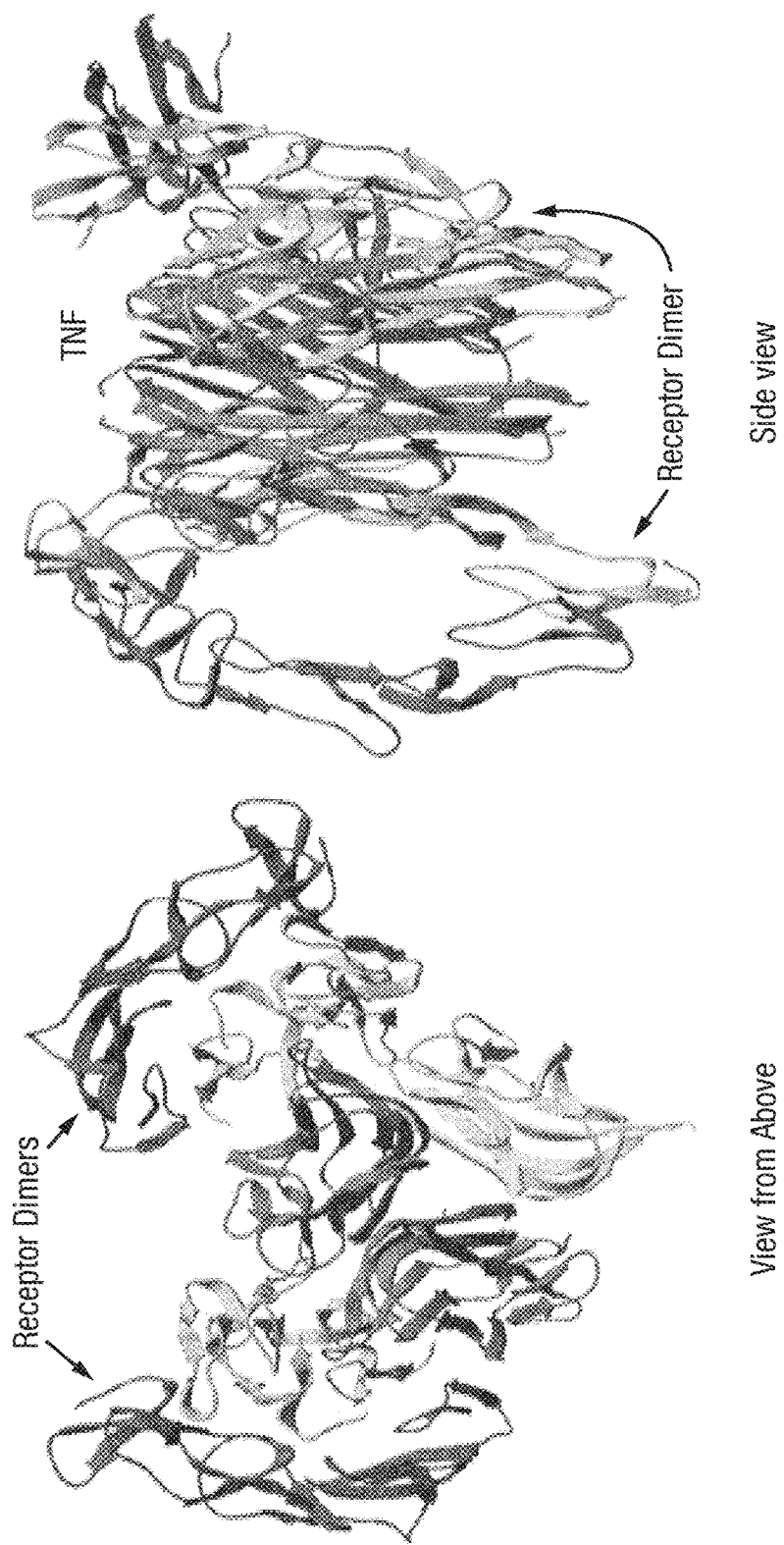
FIG. 2 shows a crystal structure with only two receptor dimers interacting with a compound-stabilised TNFα trimer.

The compounds identified using the methods of the present invention induce and/or stabilise conformational changes within the TNF trimers. These trimers have altered affinities for receptors; especially for the second and third receptors where there is reduced affinity. This reduced affinity results in a decrease in the number of receptors binding per trimer-compound complex. For example, as shown in FIG. 2 only two receptor dimers may bind per trimer-compound complex (instead of the three receptors that would bind under normal conditions).

Figure 3:
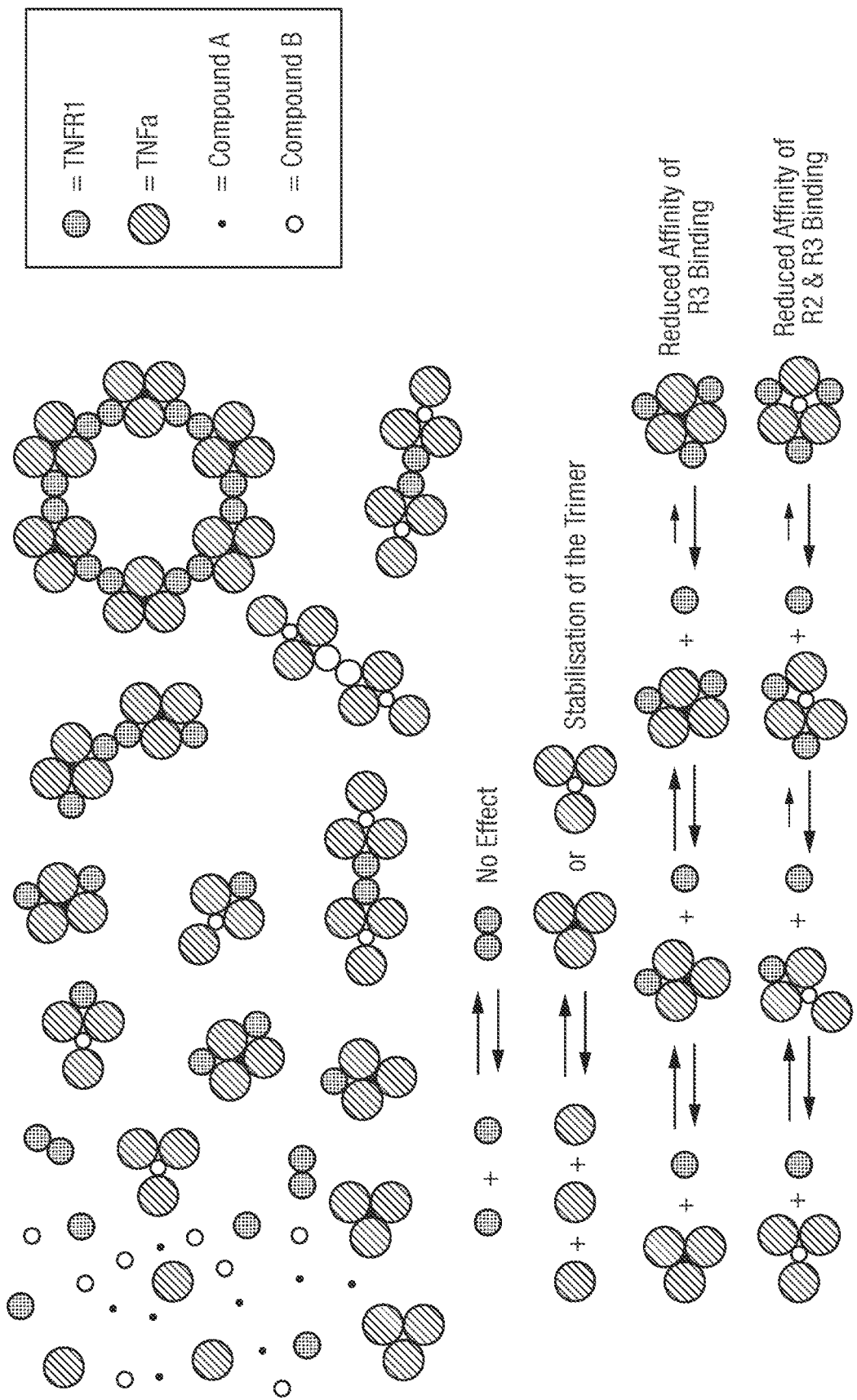
FIG. 3 shows the effects of two types of compounds (A and B) on TNFα/TNF-R1 signalling. Both compounds have no effect on the formation of receptor dimers, but induce and/or stabilise formation of trimers with distorted conformations. Trimers with the first type of compound (A) bind the first and second receptor, but have a reduced affinity for the third receptor. Accordingly, trimers form with only two receptors bound. Trimers with the second compound (B) bind the first receptor, but have a reduced affinity for the second and third receptors. Trimers therefore form with only one receptor bound. The decrease in the number of receptors binding per trimer interferes with raft formation.
Figure 4A:
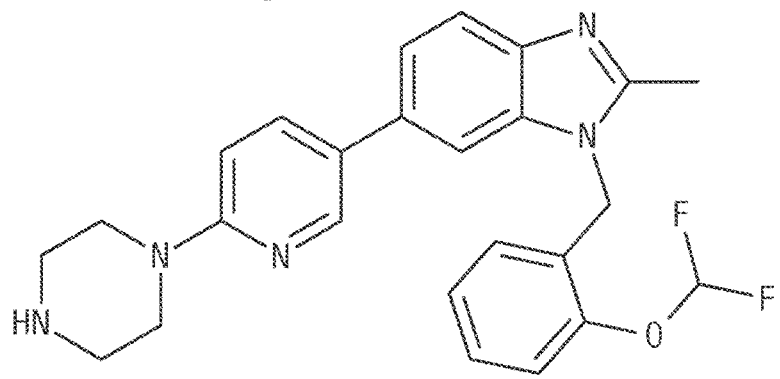
FIG. 4A shows the structure of a compound of formula (1)
Figure 4B:
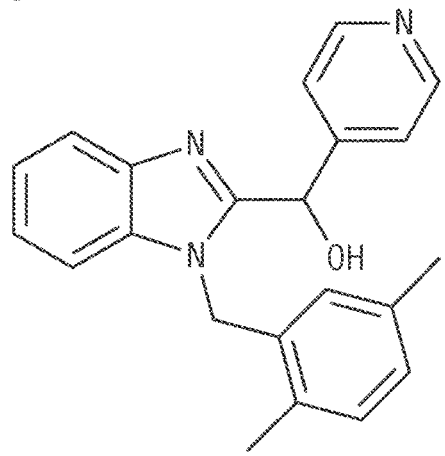
FIG. 4B shows the structure of a compound of formula (2)
Figure 4C:
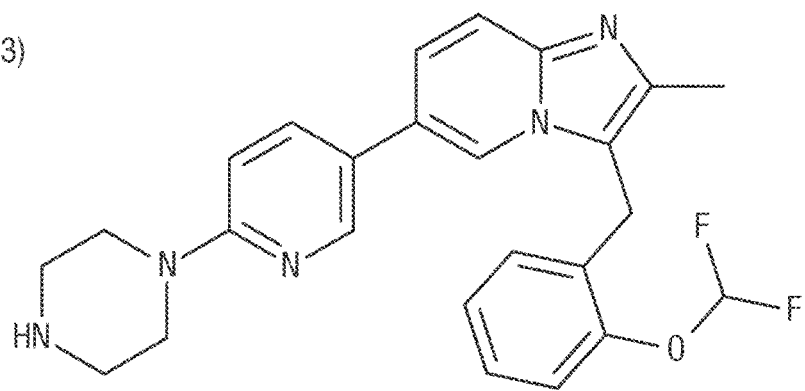
FIG. 4C shows the structure of a compound of formula (3)
Figure 4D:
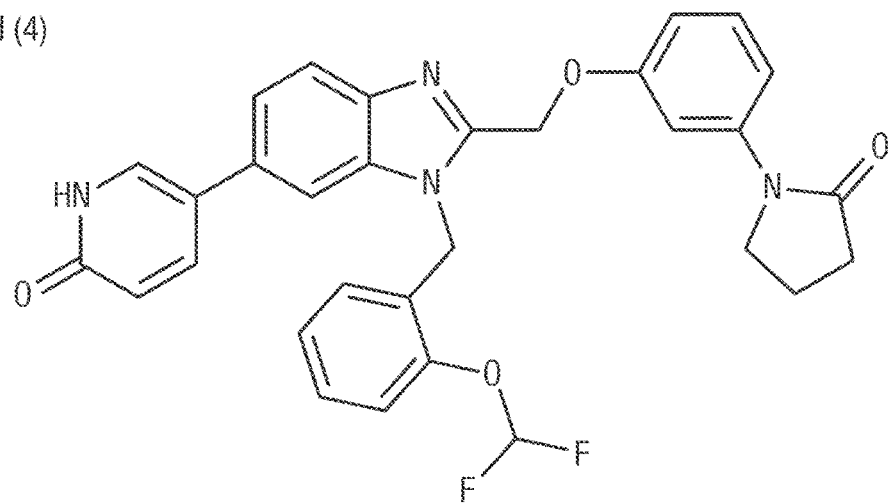
FIG. 4D shows the structure of a compound of formula (4) and FIG. 4E shows the structure of a compound of formula (5).
Figure 4E:
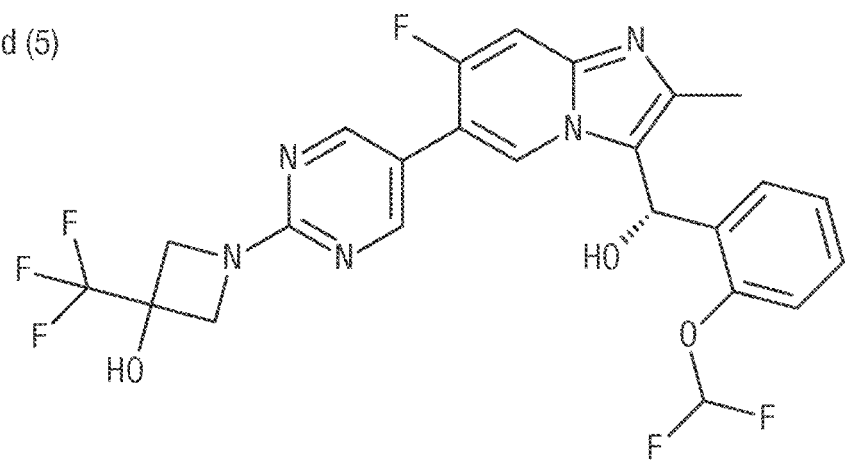
Figure 8A:
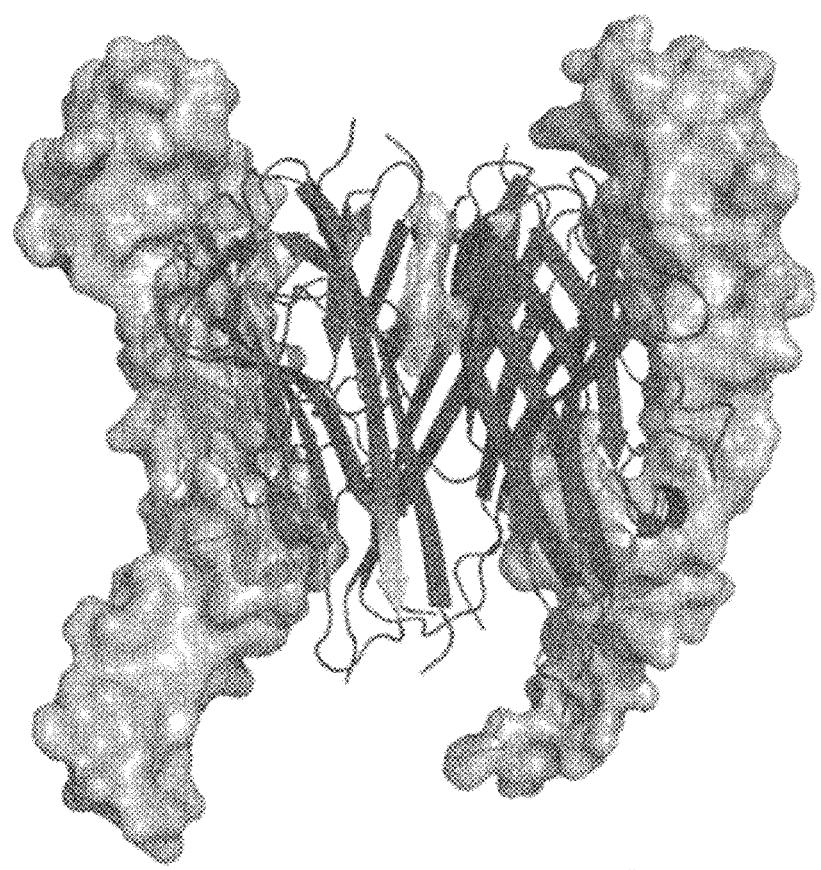
FIGS. 8A-8D show the results of crystallography experiments, which reveal two receptors binding per trimer-compound complex in the presence of compound (1). Parts (A)-(D) are alternate views of the same crystal structure.
Figure 8B:
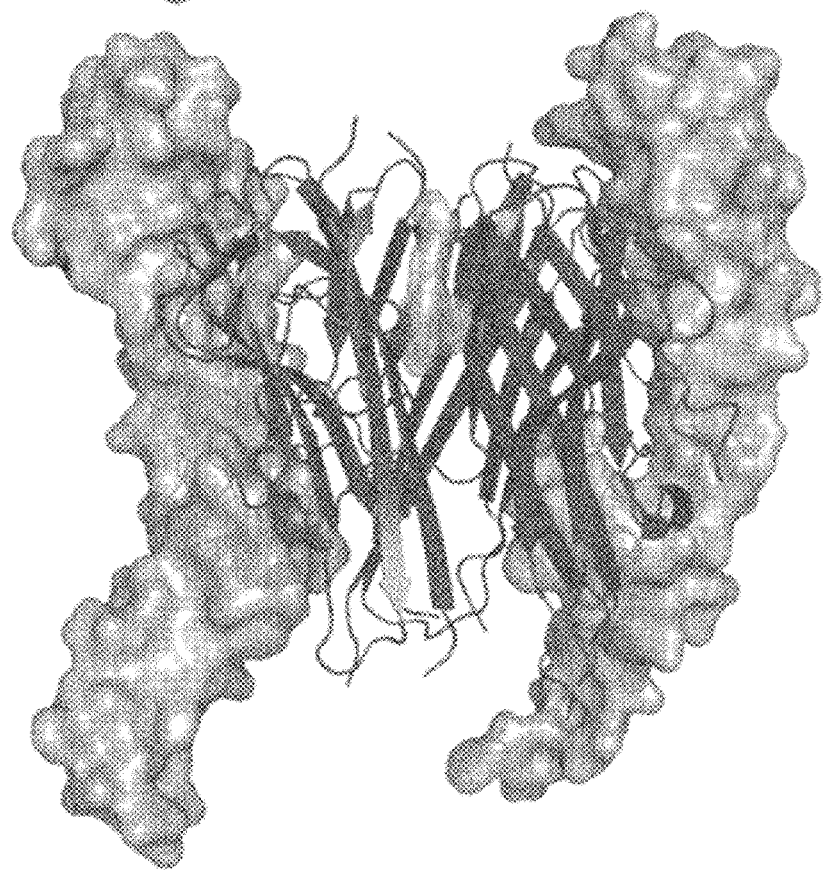
Figure 8C:
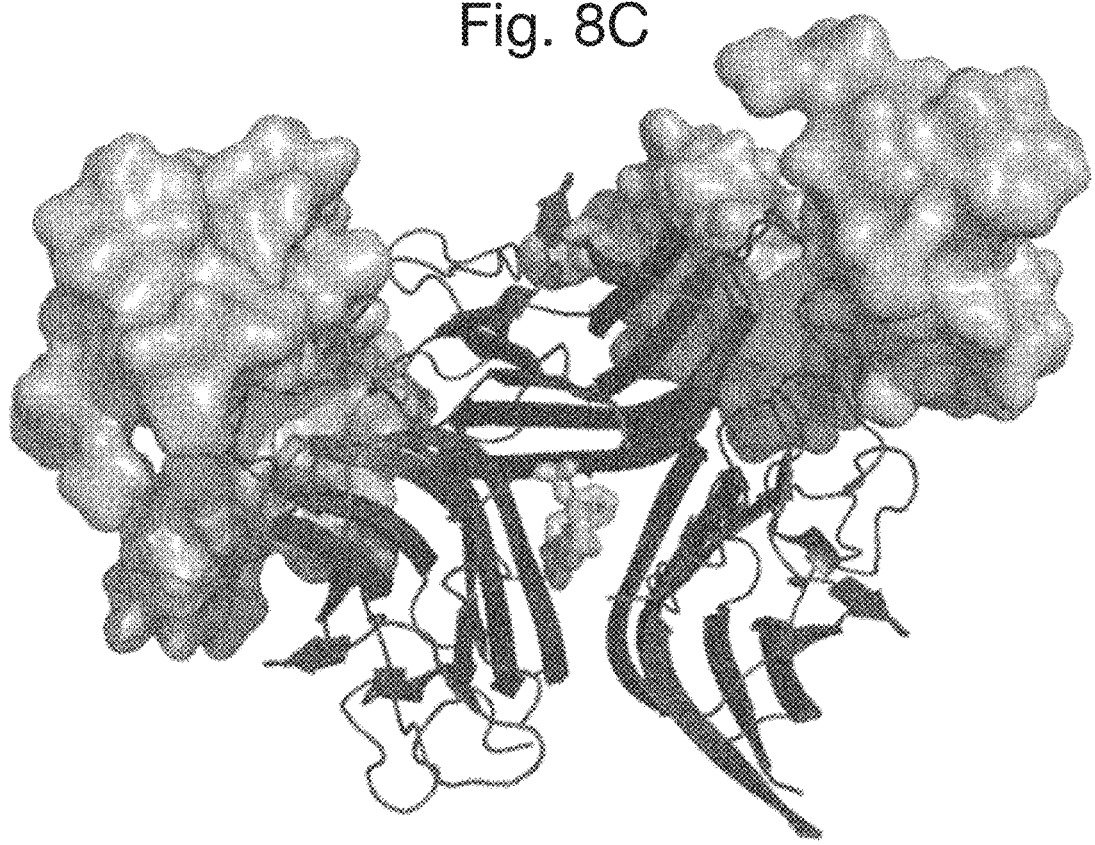
Figure 8D:
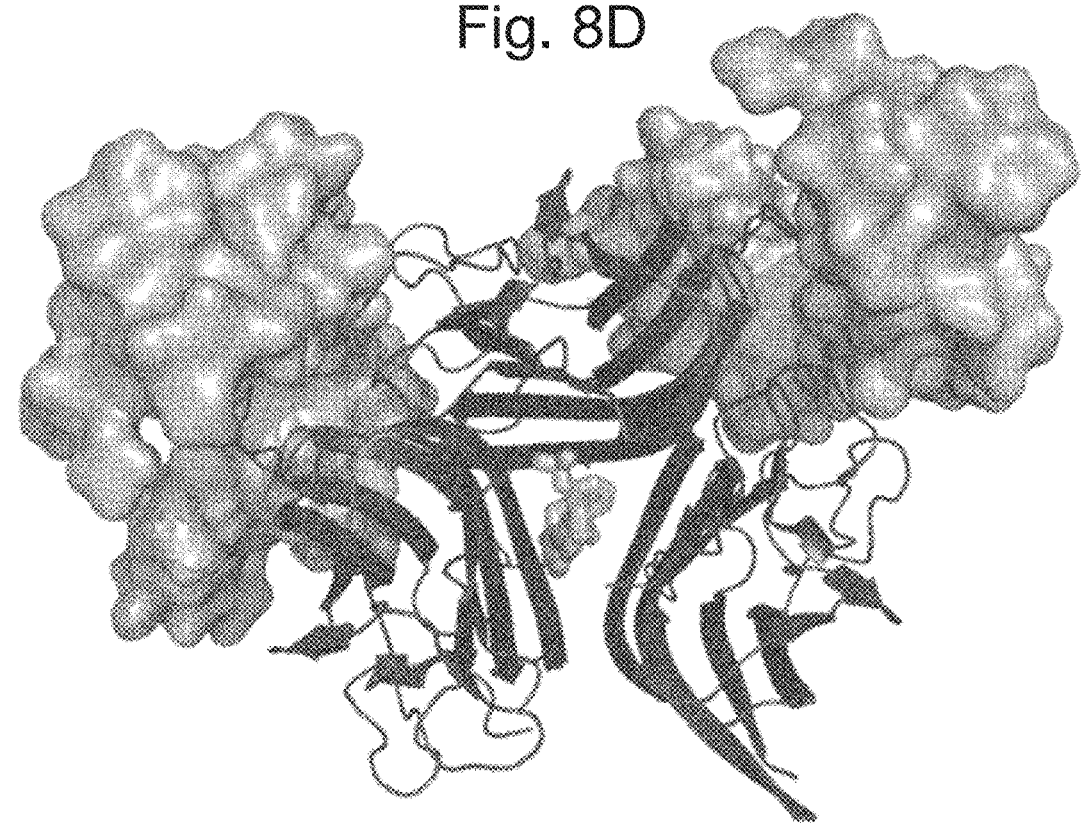

FIG. 3 shows the effects of two types of compounds on TNFα/TNF-R1 signalling. Both compounds have no effect on the formation of receptor dimers, but induce and/or stabilise formation of trimers with distorted conformations. Trimers with the first type of compound bind the first and second receptor, but have a reduced affinity for the third receptor. Accordingly, trimers form with only two receptors bound. Trimers with the second compound bind the first receptor, but have a reduced affinity for the second and third receptors. Trimers therefore form with only one receptor bound. Both types of compound thus interfere with the formation of signalling rafts due to the decrease in the number of receptors binding per trimer In view of this, the methods of the present invention involve determining the average number of receptors bound per trimer-compound complex in order to identify compounds which modulate TNF signalling. The term "average" reflects the fact that a mixed population of trimers/receptors will almost certainly be present in a sample. For example, as some compounds reduce the affinity of trimers for receptor three, some trimers may still bind all three receptors in the presence of the compound, but the majority of trimers will only have two receptors bound.

The term "average" may refer to a modal value, i.e. the number of receptors bound per trimer-compound complex which occurs most frequently within a sample. A modal value may be determined visually from experimental results. This is illustrated in the Examples section below.

It is also possible to resolve experimental data in order to identify a quantitative measurement of the proportion (percentage) of trimers in a sample with three, two, one or zero receptors bound. Such methods are routine in the art. For example, using size exclusion chromatography it is possible to resolve peaks at different elution volumes, each corresponding to trimers with a different number of receptors bound. Areas under the peaks can then be calculated and the areas used to determine the proportions (percentages) of trimers in a sample binding three, two, one or zero receptors. A modal average then refers to the number of receptors binding per trimer which occurs at the highest percentage.

The term "average" may also refer to a mean value.

To illustrate both modal and mean average values, if a method (such as those described below) identifies that 5% of trimers present in a sample have 1 receptor bound, 75% have two receptors bound, and 20% have three receptors bound, the modal value will be two receptors bound per trimer. The mean value will be 2.15 receptors bound per trimer ((5×1+75×2+20×3)/100).

When determining mean values in this way, a result of 0-0.4 is taken to indicate that on average zero receptors are bound per trimer, a result of 0.5-1.4 is taken to indicate that on average one receptor is bound per trimer, a result of 1.5-2.4 is taken to indicate that on average two receptors are bound per trimer and a result of greater than 2.5 is taken to indicate that on average three receptors are bound per trimer.

In the methods of the invention, the average number of receptors bound per trimer-compound complex is typically determined in comparison to a control. The control sample is treated in the same way as the sample with the test compound. In particular, the control sample is subjected to the same experimental conditions as the sample comprising the test compound, including the same concentrations of reagents, trimers and receptors. Furthermore, the average number of receptors bound per trimer for the control is determined using the same experimental method as for the test compound.

The average number of receptors bound per trimer is usually determined at the same time for the test sample and for the control. In other words, the experiments are run in parallel. However, values for the average number of receptors bound per trimer in a control may also be determined prior to performing experiments on the test sample. Such values may be recorded e.g. on a computer.

In order to allow an effective comparison between the results, the average number of receptors bound per trimer for a control is calculated in the same way as for the test sample (i.e. modal values or mean values as discussed above).

The control sample may comprise TNF superfamily member trimers and the requisite receptors in the absence of compound (a negative control). In other words, the control sample is identical to the test compound sample, except there is no test compound present. The TNF superfamily member trimers and the requisite receptors may be any of those discussed above, but are the same in the control and test sample (and are present at the same concentrations).

Preferably, when the control sample comprises TNF superfamily member trimers and the requisite receptors in the absence of compound, a decrease/reduction in the average number of receptors bound per trimer-compound complex in the test sample in comparison to the control identifies that the compound is capable of modulating signalling through the receptor. In other words, a test compound is identified as being capable of modulating signalling of the trimeric protein through the receptor if a lower number of receptors are identified as being bound on average per trimer in the sample with the test compound compared with the control sample.

For example, when calculated using a modal value if the control is determined to have an average of three receptors bound per trimer, a test compound may be identified as being capable of modulating signalling if two or fewer receptors are determined to be bound on average per trimer-compound complex. A negative control comprising TNF superfamily member trimers, and the requisite receptors, in the absence of compound should be found to bind an average of three receptors per trimer (when the receptors are present at an equivalent concentration or in an excess compared with the TNF monomers; at a molar ratio of at least 1:1 (receptors: monomers) or 3:1 (receptors:trimers)). Nevertheless, if the control is identified as having an average of two receptors bound per trimer, a test compound will be identified as being capable of modulating signalling if one or zero receptors are determined to be bound on average per trimer-compound complex. Finally, if the control is identified as having an average of one receptor bound per trimer, a test compound will be identified as being capable of modulating signalling if zero receptors are determined to be bound on average per trimer-compound complex.

The same reasoning applies when using mean values as the average, as calculated above.

A decrease in the average number of receptors bound per trimer, relative to the negative control, can also simply be calculated based on the percentage of trimers in a sample binding three, two, one or zero receptors. In this case, it is first necessary to identify the percentage of trimers in both the control sample and the sample containing the test compound having three, two, one or zero receptors bound. A test compound is then identified as being capable of modulating signalling if the presence of the compound results in a change in the percentage of trimers having a certain number of receptors bound. Such calculations are typically based on the percentage of trimers in a sample having three receptors bound, where a decreased percentage of trimers having three receptors bound would be indicative of an antagonist compound that modulates signalling (the percentage of trimers binding two, one or zero receptors must concurrently increase).

To illustrate, in a negative control comprising receptors and trimers only (without compound) 90% of trimers may be found to bind three receptors and 10% of trimers may be found to bind two receptors. A test compound may then be identified as being capable of modulating signalling if the compound results in less than 90% of trimers binding three receptors. If a lower percentage of trimers are binding three receptors, the percentage of trimers binding two, one or zero receptors must have increased. Accordingly, the average number of receptors bound per trimer-compound complex is decreased relative to the control.

Preferably, a test compound is identified as being capable of modulating signalling if in the test compound sample the percentage of trimers having three receptors bound is decreased by at least 10% (i.e. at least 10% lower), at least 20%, at least 30%, at least 40%, at least 50%, at least 60%, at least 70%, at least 80%, at least 90%, or at least 95% compared with the percentage of trimers having three receptors bound in the negative control sample (comprising the TNF superfamily member and receptors in the absence of compound).

Alternatively, the control may comprise TNF superfamily member trimers, the requisite receptors, and a compound which is known to modulate signalling through the receptors (a so called "positive control"). The compound which is known to modulate signalling through the receptor may be any compound known to decrease the average number of receptors bound per trimer to two, one, or zero (under conditions where the trimers would bind three receptors in the absence of any compound). Such compounds can be identified using the methods described herein. Examples of compounds known to decrease the average number of receptors to two per trimer are compounds (1)-(4) and an example of a compound known to decrease the average number of receptors to closer to one per trimer is compound (5). The positive control may comprise any one of these exemplary compounds.

As described above, the positive control sample is treated in the same way as the sample with the test compound and the same experimental conditions, methods and calculations are used for both the control sample and test compound sample. The average number of receptors bound per trimer-compound complex is usually determined at the same time for the test compound sample and for the control, but could also be determined prior to performing experiments on the test compound sample.

Preferably, when the positive control sample comprises TNF superfamily member trimers, the requisite receptors, and a compound which is known to be capable of modulating signalling through the receptor, an equivalent average number of receptors bound per trimer-compound complex in the test sample in comparison with the control, or decrease in the average number of receptors bound per trimer-compound complex in the test sample in comparison with the control, identifies that the compound is capable of modulating signalling through the receptor. In other words, a test compound is identified as being capable of modulating signalling of the trimeric protein through the receptor if an identical or lower number of receptors are on average identified as being bound per trimer in the sample with the test compound compared with the positive control.

For example, when calculated using a modal value (described above) if the positive control is determined to have an average of two receptors bound per trimer, a test compound will be identified as being capable of modulating signalling if two or fewer receptors (two receptors, one receptor or zero receptors) are determined to be bound on average per trimer-compound complex. Likewise, if the control is identified as having an average of one receptor bound per trimer, a test compound will be identified as being capable of modulating signalling if one or zero receptors are determined to be bound on average per trimer-compound complex. If the control is identified as having an average of zero receptors bound per trimer, a test compound will be identified as being capable of modulating signalling if zero receptors are also determined to be bound on average per trimer-compound complex.

The same reasoning applies when using mean values as the average.

An equivalent average number of receptors bound per trimer, or a decrease in the average number of receptors bound per trimer, in comparison with a positive control can again also be calculated using the proportions (percentages) of trimers in a sample binding three, two, one or zero receptors. As described above, it is first necessary to identify the percentage of trimers in both the control sample and the sample containing the test compound having three, two, one or zero receptors bound. A test compound is then identified as being capable of modulating signalling if the presence of the compound results in an equivalent percentage, or increased/higher percentage, of trimers having the desired number of receptors bound (or a lower number of receptors bound) in comparison with the control. Such calculations may be focused on the percentage of trimers in a sample having two or fewer receptors bound, one or fewer receptor bound, or zero receptors bound.

To illustrate, in a positive control sample a compound may result in 30% of the trimers present binding three receptors and 70% of the trimers present binding two receptors. A test compound may then be identified as being capable of modulating signalling if the compound results in at least 70% percent of the trimers present binding two or fewer (two, one or zero) receptors.

"An equivalent percentage" in this context typically refers to values which are within 10% or less of each other, preferably 5% or less. For example, a test compound which results in 70% of trimers binding two receptors can be seen as resulting in an equivalent percentage of trimers binding two receptors as a control where 75% of trimers bind two receptors.

A compound may also be identified as being capable of modulating signalling simply based on determination of the number of receptors binding per trimer-compound complex, without a direct comparison to a control.

In this scenario, a compound may be identified as being capable of modulating signalling of the trimeric protein through the receptor if an average of less than three receptors are determined to be bound per trimer-compound complex. The average number of receptors bound per trimer-compound complex may be a mean value or a modal value as described above. Compounds are preferably identified as being capable of modulating signalling of the trimeric protein through the receptor if the compound results in an average of two receptors binding per trimer. More preferably, a compound is identified as being capable of modulating signalling of the trimeric protein through the receptor if the compound results in an average of one receptor binding per trimer. A compound may also be identified as being capable of modulating signalling of the trimeric protein through the receptor if the compound results in an average of zero receptors binding per trimer. Examples of such compounds are discussed in more detail below.

The average number of receptors binding per trimer-compound complex is typically determined at approximately an equivalent concentration (a 1:1 molar ratio) of receptors to TNF monomers. A 1:1 ratio of receptors:momoners corresponds to a 3:1 ratio of receptors:trimers.

The concentration of receptors may be in a slight excess compared with the concentration of monomers. Experiments are preferably conducted at a molar ratio of up to approximately 10:1 (receptors:trimers). Experiments may be conducted at any molar ratio within a range of between approximately 3:1 and 10:1 (receptors:trimers). Preferably, assays are conducted at ratios of approximately 3:1, 4:1, 5:1: 6:1, 7:1, 8:1, 9:1 or 10:1 (receptors:trimers). In some cases, assays are conducted at multiple concentrations of receptors:trimers e.g. approximately 3:1, 6:1 and 10:1. These titrations are illustrated in more detail in the Examples section.

Typically, experiments to determine the average number of receptors binding per trimer-compound complex are carried out when the compound is present at a concentration of compound that ensures complete occupancy of the trimers with compound. As discussed below, occupancy of the trimers with compound may be determined using mass spectrometry. The compound may be present at an equal concentration compared with the concentration of trimers (a 1:1 ratio of compound:trimers; a 1:3 ratio of compound:TNF monomers). The compound is, however, typically present in an excess relative to the concentration of the TNF trimers. For example, the compound may be present in an excess of between 1.5× and 500× relative to the concentration of trimers. Preferably, the compound is present in an excess of between 5× and 100× relative to the concentration of trimers, more preferably in an excess of between 10× and 50× relative to the concentration of trimers. The compound may be present at an excess of at least 1.5×, at least 2×, at least 3×, at least 4×, at least 5×, at least 6×, at least 7×, at least 8×, at least 9×, at least 10×, at least 20×, at least 50×, at least 100×, at least 250× or at least 500× relative to the concentration of TNF trimers.

Experiments may be carried out with a range of concentrations of compound, as shown in the Examples below.

The average number of receptors binding per trimer may be determined using any suitable technique, for example using ion mobility mass spectrometry, size exclusion chromatography, an aggregation assay, Förster Resonance Energy Transfer and/or crystallography. These techniques may be used alone or, preferably, in combination in order to determine the average number of receptors binding per trimer. For example, any two three, four or all five of the techniques may be used together.

Ion mobility mass spectrometry (IMS-MS) combines ion-mobility spectrometry and mass spectrometry in order to identify components within a test sample. Methods for conducting IMS-MS, and for resolving the obtained data, are well known in the art and are illustrated further in the Examples section below.

In an exemplary procedure, the test compound is incubated with TNF overnight at room temperature. A native mass spectrum is first recorded to ensure that the compound has 100% occupancy of the TNF prior to addition of the compound. In other words, the native mass spectrum ensures that the compound is binding to the trimers. The compound is typically present in an excess relative to the concentration of trimers, as described above. The requisite TNF receptors are then added and incubated before the ion mobility mass spectrum of the sample is collected.

Ion mobility mass spectrometry assays are conducted at any suitable ratio of receptors:trimers, typically at approximate ratios of between 3:1 and 10:1, for example 3:1, 6:1 and/or 10:1 (receptors:trimers). In many cases, ion mobility mass spectrometry assays are conducted at a number of concentration ratios for a test sample.

Ion mobility mass spectrometry can also be used to provide affinity data for binding of the three receptors to TNF trimers. This is illustrated in the Examples section below.

Another technique that can be used to determine the number of receptors binding on average per TNF trimer is size exclusion chromatography. Size exclusion chromatography methods are well known in the art, and involve separating components in a solution based on their size. Smaller components in the solution elute more slowly and require a larger elution volume in comparison to larger components.

A TNF trimer binding three receptors will be larger than a trimer binding only two receptors. Trimers binding three receptors are therefore eluted at a smaller volume compared with trimers binding two receptors or one receptor. The peaks at different elution volumes can thus be used to identify the average number of receptors bound per trimer. This is illustrated in more detail in the Examples section below.

In an exemplary size exclusion chromatography procedure, the TNF trimers are incubated with an excess of compound. Occupancy of the TNF trimers with compound can be determined by IMS-MS, as described above. The samples are then incubated with receptors, and analysed by size exclusion HPLC.

Typically, size exclusion chromatography experiments are conducted at approximate ratios of between 3:1 and 10:1, for example 3:1, 6:1 and/or 10:1 receptors:trimers. Preferably, a compound is tested at a range of concentration ratios.

Controls to establish the migration (peak) positions for trimers with two receptors bound, or one receptor bound, are illustrated in the Examples section below. These controls comprise mutant TNFα, which has impaired binding of either the third, or second and third, receptors.

Another technique which may be used to determine the average number of receptors binding per TNF trimer is an aggregation assay.

Another suitable assay for determining the average number of receptors bound per trimer is Förster Resonance Energy Transfer (FRET). FRET can be used to determine whether two fluorophores (donor and acceptor) are within close proximity to each other.

In the assay of the present invention, the receptors may be tagged with e.g. the donor fluorophore. The trimers are then tagged with e.g. the acceptor fluorophore (possibly via a linker). Experiments are typically conducted at a ratio of 1:1 receptors:monomers, but receptor titrations may also be performed. Likewise, experiments may be performed with the test compound present at a variety of concentrations. This is illustrated in the Examples below.

Finally, crystallography may be used in order to determine the average number of receptors binding per trimer. Crystallography techniques are well known in the art.

All of the methods of the invention involve providing an output that identifies that the compound is capable of modulating signalling through the receptor. The output may be recording information e.g. in a laboratory notebook. The output may also be recording information on a computer.

Compounds and Complexes

The present invention also relates to compounds that are capable of binding to a trimeric protein that is a TNF superfamily member and modulating signalling of the TNF superfamily member through the requisite receptor. The compounds result in corresponding average number, or a change in the average number, of receptors bound per trimer-compound complex in comparison with a control. Such compounds may be identified by the methods described above.

The TNF superfamily members and requisite receptors may be any of those described above.

Compounds can readily be screened for binding to a TNF trimer using routine methods known in the art, such as mass spectrometry. Mass spectrometry can also be used to identify the presence of the TNF trimers themselves in a sample.

Mass spectrometric methods may include, for example, matrix-assisted laser desorption/ionization mass spectrometry (MALDI MS), surface-enhanced laser desorption/ionization mass spectrometry (SELDI MS), time of flight mass spectrometry (TOF MS) and liquid chromatography mass spectrometry (LC MS).

The compounds are not limited in terms of their chemical formula or structure. The compounds are typically small molecular entities (SMEs) that have a molecular weight of 1000 Da or less, preferably 750 Da or less, more preferably 600 Da or less. The compounds may bind inside the central space present within the TNF superfamily member trimer (i.e. the core of the trimer). Binding of a compound within the core of the trimer can be detected using routine methods e.g. using crystallography. The compounds may comprise a benzimidazole moiety or an isostere thereof.

The compounds bind to at least one TNF superfamily member and modulate the signalling of the TNF superfamily member through the requisite receptor. Modulation of signalling is described above in the context of the methods of the present invention. At a 1:1 molar ratio of receptors: monomers, or in the presence of an excess of receptors, a TNF trimer usually binds an average of three receptors. The compounds of the present invention modulate signalling by resulting in an equivalent average number of receptors bound per trimer-compound complex, or a change in the average number of receptors bound per trimer-compound complex, in comparison with a control.

As described above, the control may comprise TNF superfamily member trimers and receptors in the absence of the compound (a negative control). The TNF superfamily member trimers and receptors are the same for both the test compound and the control, and the test compound sample and control are subjected to the same experimental conditions (e.g. concentrations of reagents) and methods.

The control may be run in parallel to the sample comprising the test compound. Alternatively, the control may be run prior to the test compound sample.

When the control comprises TNF superfamily member trimers and receptors in the absence of compound, three receptors would be expected to bind on average per trimer when assays are performed at an equivalent (1:1) molar ratio of TNF monomers:receptors, or when the receptors are present in an excess compared to the concentration of monomers. An antagonist compound results in a decrease in the average number of receptors binding per trimer under such conditions. Methods of determining a decrease in the average number of receptors binding per trimer are discussed above.

Alternatively, the control may comprise TNF superfamily member trimers, the requisite receptors, and a compound known to modulate signalling of the trimers through the receptors (a positive control). Again, the TNF superfamily member trimers and receptors are the same for both the test compound and the control, and the test compound sample and control are subjected to the same experimental conditions (e.g. concentrations of reagents) and methods. Typically, the control is run in parallel to the test compound. However, the control may also be run prior to the test compound sample.

When the control comprises TNF superfamily member trimers, the requisite receptors, and a compound known to modulate signalling of the trimers through the receptors, a compound is identified as being capable of modulating signalling if it results in an equivalent average number of receptors bound per trimer-compound complex in comparison with the control, or decrease in the average number of receptors bound per trimer-compound complex in comparison with the control. Methods of identifying compounds in this way are described above.

Antagonistic compounds result in an average of less than three receptors binding per trimer-compound complex (under conditions where in the absence of compound three receptors on average would bind per trimer-compound complex). Preferably, under such conditions a test compound results in an average of two receptors binding per trimer-compound complex. Examples of such compounds include compounds (1)-(4). These compounds can be used as positive control compounds, when evaluating whether another test compound is capable of modulating signalling.

More preferably, a test compound results in an average of one receptor binding per trimer-compound complex. Examples of such compounds include compound (5), which results in a shift towards a single receptor binding per trimer. Again, these compounds can be used as positive control compounds when evaluating whether another test compound is capable of modulating signalling.

A test compound may also result in an average of zero receptors binding per trimer-compound complex.

The present invention also relates to a complex comprising a trimeric protein that is a TNF superfamily member and a compound. The trimeric protein that is a TNF superfamily member, and the compound, may be any of those described above.

Antibodies for Identifying Trimer-Compound Complexes

The present inventors developed antibodies that bind selectively to complexes comprising compounds of the invention and a trimeric TNF superfamily member. These antibodies may be used to identify further compounds that are capable of inhibiting TNF.

In particular, the present inventors have identified two antibodies, termed CA185_01974 and CA185_01979, which were raised against human TNFα in complex with a compound of the invention. The heavy chain variable region (HCVR) of CA185_01974 is shown in SEQ ID NO: 3 and the light chain variable region (LCVR) of CA185_01974 is shown in SEQ ID NO: 4. The full length IgG1 heavy chain is shown in SEQ ID NO: 5 (1974 HC mIgG1 full) and the full length light chain (1974 LC kappa full) is shown in SEQ ID NO: 6.

The HCVR of CA185_01979 is shown in SEQ ID NO: 7 and the LCVR of CA185_01979 is shown in SEQ ID NO: 8. The full length IgG1 heavy chain of CA185_01979 is shown in SEQ ID NO: 9 (1979 HC mIgG1 full) and the full length light chain in SEQ ID NO: 10 (1979 LC Kappa full).

Antibodies comprising the above HCVR/LCVR or full-length sequence pairs can readily be generated by the skilled person using standard techniques.

Methods of the invention for determining compounds which are capable of binding to a trimeric protein which is a TNF superfamily member and modulating signalling through the receptor may therefore involve identifying whether an antibody with a HCVR/LCVR pair of SEQ ID NOs: 3/4 or 7/8 binds the trimer-compound complex. Likewise, methods may involve identifying whether an antibody with a sequence pair of SEQ ID Nos: 5/6 or 9/10 binds the trimer compound complex. Antibody assays may be used in addition to the other assays described herein.

Antibodies of the invention can be tested for binding to a compound-trimer complex by, for example, standard ELISA or Western blotting. The binding selectivity of an antibody may also be determined by monitoring binding of the antibody to cells expressing the target protein, for example by flow cytometry. Thus, a screening method of the invention may comprise the step of identifying an antibody that is capable of binding a compound-trimer complex by carrying out an ELISA or Western blot or by flow cytometry.

The antibodies described herein selectively (or specifically) recognise at least one compound-trimer complex, i.e. epitopes within a compound-trimer complex. An antibody, or other compound, "selectively binds" or "selectively recognises" a protein when it binds with preferential or high affinity to the protein for which it is selective but does not substantially bind, or binds with low affinity, to other proteins.

In the present instance, a compound-trimer complex may typically bind an antibody with a HCVR/LCVR pair of SEQ ID NOs: 3/4 or 7/8 (or with sequence pairs of SEQ ID NOs: 5/6 or 9/10) with an affinity of less than 1 nM. In other words, the methods of the invention may involve determining that a compound is capable of binding to a trimeric protein which is a TNF superfamily member and modulating signalling through the receptor by identifying that an antibody with a HCVR/LCVR pair of SEQ ID NOs: 3/4 or 7/8 (or sequence pairs of SEQ ID NOs: 5/6 or 9/10) binds the trimer-compound complex with a KD-ab of less than 1 nM. In some instances, the KD-ab may be less than 500 pM, or less than 200 pM. The affinity may be determined by surface plasmon resonance. The TNF is typically human TNFα.

Likewise, a complex of the invention may be a complex of a trimeric TNF superfamily member and a compound, wherein the compound-trimer complex binds an antibody with a HCVR/LCVR pair of SEQ ID NOs: 3/4 or 7/8 (or sequence pairs of SEQ ID Nos: 5/6 or 9/10). Again, the TNF is typically human TNF α, and the binding affinity is typically less than 1 nM (or less than 500 pM/200 pM). Binding affinity is typically determined by surface plasmon resonance.

Therapeutic Indications

TNFα is the archetypal member of the TNF superfamily. TNFα is a pleiotropic cytokine that mediates immune regulation and inflammatory responses. In vivo, TNFα is also known to be involved in responses to bacterial, parasitic and viral infections. In particular, TNFα is known to have a role in rheumatoid arthritis (RA), inflammatory bowel diseases (including Crohn's disease), psoriasis, Alzheimer's disease (AD), Parkinson's disease (PD), pain, epilepsy, osteoporosis, asthma, sepsis, fever, Systemic lupus erythematosus (SLE) and Multiple Sclerosis (MS) and cancer. TNFα is also known to have a role in Amyotrophic Lateral Sclerosis (ALS), ischemic stroke, immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AKI), obstructive uropathy, kidney allograft rejection, cisplatin-induced AKI and obstructive uropathy.

Other members of the TNF superfamily are known to be involved in autoimmune disease and immune deficiencies. In particular, members of the TNF superfamily are known to be involved in RA, SLE, cancer, MS, asthma, rhinitis, osteoporosis and multiple myeloma (MM). TL1A is known to play a role in organ transplant rejection.

A compound identified using the methods of the invention, or a TNF-trimer compound complex, may be used in a method of therapy of the human or animal body. A compound or complex may be used to treat, prevent or ameliorate any condition that that can be treated, prevented or ameliorated by a conventional TNF superfamily member modulator. The compound or complex may be used alone or in combination with a conventional TNF superfamily member modulator.

Any condition that results, partially or wholly, from pathogenic signalling through a TNF receptor by a TNF superfamily member or from a deficiency in signalling through a TNF receptor by a TNF superfamily member may in principle be treated, prevented or ameliorated according to the present invention. Pathogenic signalling through a TNF receptor by a TNF superfamily member includes increased signalling through a TNF receptor over and above the normal physiological level of signalling, signalling through a TNF receptor which is initiated normally, but which fails to stop in response to normal physiological signals and signalling through a TNF receptor that is within the normal physiological range of magnitude, but which is initiated by non-physiological means. In a preferred embodiment, the invention relates to the treatment, prevention or amelioration of conditions mediated or influenced by TNFα.

The compounds that interact with TNFα are accordingly beneficial in the treatment and/or prevention of various human ailments. These include autoimmune and inflammatory disorders; neurological and neurodegenerative disorders; pain and nociceptive disorders; and cardiovascular disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis, spontaneous infertility, osteoporosis, asthma and muscular dystrophy (including Duchenne muscular dystrophy).

Neurological and neurodegenerative disorders include Alzheimer's disease, Parkinson's disease, Huntington's disease, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction).

In particular, a compound or a complex may be used to treat or prevent inflammatory disorders, CNS disorders, immune disorders and autoimmune diseases, pain, osteoporosis, fever and organ transplant rejection. In a preferred embodiment, a compound or a complex may be used to treat or prevent rheumatoid arthritis, inflammatory bowel diseases (including Crohn's disease), psoriasis, Alzheimer's disease, Parkinson's disease, epilepsy, asthma, sepsis, systemic lupus erythematosus, multiple sclerosis, asthma, rhinitis, cancer and osteoporosis. In another preferred embodiment, a compound or a complex may be used to treat or prevent rheumatoid arthritis (RA), non specific inflammatory arthritis, erosive bone disease, chondritis, cartilage degeneration and/or destruction, juvenile inflammatory arthritis, Still's Disease (juvenile and/or adult onset), juvenile idiopathic arthritis, juvenile idiopathic arthritis (both oligoarticular and polyarticular forms), inflammatory bowel diseases (including Crohn's disease, ulcerative colitis, indeterminate colitis, pouchitis), psoriasis, psoriatic arthopathy, ankylosing spondylitis, Sjogren's Disease, Alzheimer's disease (AD), Behcet's Disease, Parkinson's disease (PD), amyotrophic lateral sclerosis (ALS), ischemic stroke, pain, epilepsy, osteoporosis, osteopenia, anaemia of chronic disease, cachexia, diabetes, dyslipidemia, metabolic syndrome, asthma, chronic obstructive airways (or pulmonary) disease, sepsis, fever, respiratory distress syndrome, systemic lupus erythematosus (SLE), multiple sclerosis (MS) immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AKI), obstructive uropathy, kidney allograft rejection, cisplatin-induced AKI and obstructive uropathy, eye diseases (including diabetic retinopathy, diabetic macular oedema, retinopathy of prematurity, age related macular degeneration, macular oedema, proliferative and/or non proliferative retinopathy, corneal vascularisation including neovascularization, retinal vein occlusion, various forms of uveitis and keratitis), thryoiditis, fibrosing disorders including various forms of hepatic fibrosis, various forms of pulmonary fibrosis, systemic sclerosis, scleroderma, cancer and cancer associated complications (including skeletal complications, cachexia and anaemia).

Pharmaceutical Compositions, Dosages and Dosage Regimes

Compounds identified using the methods of the invention and compound-trimer complexes will typically be formulated into pharmaceutical compositions, together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. In a preferred embodiment the carrier is suitable for oral administration. Depending on the route of administration, the modulator may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be preferable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients.

Also within the scope of the present invention are kits comprising compounds or complexes and instructions for use. The kit may further contain one or more additional reagents, such as an additional therapeutic or prophylactic agent as discussed above.

The compounds and the compound-trimer complexes or formulations or compositions thereof may be administered for prophylactic and/or therapeutic treatments.

In therapeutic applications, compounds and compound-trimer complexes are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is preferred.

A compound or a compound-trimer complex may be administered via one or more routes of administration using one or more of a variety of methods known in the art. As will be appreciated by the skilled artisan, the route and/or mode of administration will vary depending upon the desired results. Examples of routes of administration for compounds or compound-trimer complexes of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, a compound identified by the methods of the invention or a compound-trimer complex of the present invention of the invention can be administered via a non-parenteral route, such as a topical, epidermal or mucosal route of administration. In a preferred embodiment the compound identified by the methods of the invention or a compound-trimer complex of the invention is for oral administration.

A suitable dosage of a compound or a compound-trimer complex may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the antagonist in the patient and the duration of treatment desired.

As mentioned above, compounds or compound-trimer complexes may be co-administered with one or other more other therapeutic agents. For example, the other agent may be an analgesic, anaesthetic, immunosuppressant or anti-inflammatory agent.

Combined administration of two or more agents may be achieved in a number of different ways. Both may be administered together in a single composition, or they may be administered in separate compositions as part of a combined therapy. For example, the one may be administered before, after or concurrently with the other.

The following Examples illustrate the invention.

EXAMPLES

Example 1(A)—Synthesis of the Compounds of Formulae (1), (2), (3) and (4)

Synthesis of compound (1) is disclosed in WO 2013/186229 (Example 490).

Synthesis of compound (2) is disclosed in WO 2013/186229 (Example 2).

Synthesis of compound (3) is disclosed in WO 2014/009295 (Example 4).

Synthesis of compound (4) is disclosed in WO 2013/186229 (Example 89).

Example 1(B)—Synthesis of the Compound of Formula (5)

Nomenclature

Compounds were named with the aid of ACD/Name Batch (Network) ver. 12.0 or Accelrys Draw 4.0

Abbreviations

DCM: Dichloromethane EtOAc: Ethyl acetate
DMF: N,N-Dimethylformamide MeOH: Methanol
DMSO: Dimethylsulfoxide $SiO_2$: Silica
Et20: Diethyl ether h: Hour
THF: Tetrahydrofuran RT: retention time
r.t.: Room temperature MeCN: Acetonitrile
br.: Broad M: Mass
Brine: Saturated aqueous sodium chloride solution
HPLC: High Performance Liquid Chromatography
LCMS: Liquid Chromatography Mass Spectrometry
ES+: Electrospray Positive Ionisation
TEA: Triethylamine
TLC: thin layer chromatography Analytical Conditions All NMRs were obtained either at 300 MHz or 400 MHz.

All reactions involving air or moisture-sensitive reagents were performed under a nitrogen atmosphere using dried solvents and glassware.

All compound LCMS data were determined by using the method below.

Method 1:

Waters Acquity-SQD, Waters Acquity UPLC BEH C18, 2.1×50 mm, 1.7 μm column

Mobile phase A: 10 mM Ammonium Formate+0.1% Ammonia

Mobile phase B: 95% MeCN+5% $H_2O$+0.1% Ammonia

Gradient program (Flow Rate 1.0 mL/min, Column Temperature 40° C.):

| Time | A % | B % |
|---|---|---|
| 0.00 | 95 | 5 |
| 0.50 | 95 | 5 |
| 1.75 | 5 | 95 |
| 2.00 | 5 | 95 |
| 2.25 | 95 | 5 |

It will be apparent to the one skilled in the art that different retention times (RT) may be obtained for LCMS data if different analytical conditions are used.

Optical rotations were measured using an Optical Activity PolAAR 2001 polarimeter.

Intermediate 1

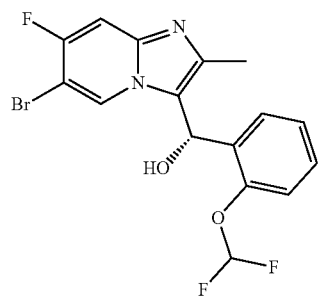 [SMILES: Cc1nc2cc(F)c(Br)cn2c1[C@@H](O)c1ccccc1OC(F)F]

(6-Bromo-7-fluoro-2-methylimidazo[1,2-a]pyridin-3-yl)[2-(difluoromethoxy)phenyl]-methanol—Enantiomer A The racemic title compound was prepared following the procedure described in patent application WO 2014/009295. The racemic mixture thus prepared was separated into the constituent enantiomers by chiral chromatography as detailed below:

The title compound was isolated by purification of racemic (6-Bromo-7-fluoro-2-methylimidazo[1,2-a]pyridin-3-yl)[2-(difluoromethoxy)phenyl]-methanol under LC conditions on Chiralpak AD (100*500 mm*mm, flow 300 mL/min, 30° C., 2-PrOH/heptane 1/9, injection of 230 mL solution at a concentration of 7.5 g/L). The first eluting enantiomer (RT 27 min) was collected and the fractions were evaporated to yield enantiomer A. [α]-12.8°. The second eluting enantiomer (RT 50 min) was collected and the fractions were evaporated to yield enantiomer B. [α]+12.7°

Intermediate 2

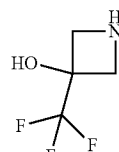

3-(trifluoromethyl)azetidin-3-ol

To a solution of 1-boc-3-azetidinone (11.3 g, 58.4 mmol) and (trifluoromethyl)trimethylsilane (9.22 g, 64.3 mmol) in THF (100 mL) cooled to ~-5° C. on an ice/brine bath was added portion wise caesium fluoride (9.77 g, 64.3 mmol). The resultant mixture was allowed to stir at r.t, TLC analysis after 4 hours at indicated complete consumption of starting material and a less polar component. The reaction was quenched by the addition of saturated aqueous ammonium chloride solution (100 mL) and the aqueous phase extracted with EtOAc (3×100 mL). The organic phase was separated, dried over sodium sulphate, filtered and the volatiles were removed in vacuo to give a crude oil. The oil thus obtained was dissolved in DCM (100 mL) and trifluoroacetic acid (40 mL) added. The mixture was stirred at ambient temperature for 4 hr. The volatiles were removed in vacuo and the residue azeotroped with toluene (3×150 mL) to give the title compound trifluoroacetate salt as a brown solid (15 g). ¹H NMR (400 MHz, d₆ DMSO): δ/ppm 9.48 (s, 2 H), 7.95 (d, J 0.3 Hz, 1 H), 4.28 (d, J 13.1 Hz, 2 H), 4.06 (m, 2 H).

The compound thus obtained was used in the subsequent reaction without further purification.

Intermediate 3

1-[5-(4,4,5,5-tetramethyl-1,3,2-dioxaborolan-2-yl)pyrimidin-2-yl]-3-(trifluoromethyl)azetidin-3-ol To a solution of Intermediate 2 (12 g) in acetonitrile (150 mL) was added TEA (30 mL) and 2-chloro-5-(4,4,5,5-tetramethyl-1,3,2-dioxaborolan-2-yl)pyrimidine (16 g) and the reaction stirred at 65° C. for 18 hours. The solvents were removed in vacuo and the solid residue triturated and washed with distilled water to give a beige solid and dried under high vacuum to give the title compound as a beige solid (18.5 g). ¹H NMR (300 MHz, d₆ DMSO): δ/ppm 8.53 (2H, s), 7.46 (1H, s), 4.33-4.31 (2H, m), 4.10-4.08 (2H, m), 1.29 (12H, s). LCMS (ES⁺) RT 1.14 min, 346.0 (M+H)⁺.

Compound (5)

1-[5-[3-[(S)-[2-(difluoromethoxy)phenyl]-hydroxymethyl]-7-fluoro-2-methyl-imidazo[1,2-a]pyridin-6-yl]pyrimidin-2-yl]-3-(trifluoromethyl)azetidin-3-ol (Enantiomer A)

A mixture of Intermediate 1 (0.7 g, 2 mmol), Intermediate 3 (0.7 g, 2 mmol), 1,1'-bis(diphenylphosphino)ferrocenepalladium(II)dichloride dichloromethane complex (36 mg, 0.044 mmol) and 2 M sodium carbonate (2 mL) in dioxane (12 mL) was de-gassed and refluxed for 3 h. The cooled reaction mixture was diluted with EtOAc, washed twice with brine, the organic layer was dried (MgSO₄) and concentrated in vacuo. The residue was columned flash column chromatography (SiO₂, 0-90% EtOAc/heptane), yielding the title compound as a cream solid (500 mg, 50%). ¹H NMR (300 MHz, DMSO-d6): δ 8.51 (m, 3H), 7.95 (dd, J₁ 2.3 Hz, J₂ 6.7 Hz, 1 H), 7.46 (m, 2 H), 7.36 (m, 2 H), 7.12 (m, 2 H), 6.42 (d, J 4.4 Hz, 1 H), 6.18 (d, J 4.4 Hz, 1 H), 4.35 (m, 2 H), 4.13 (d, J 10.2 Hz, 2 H), 2.12 (s, 3 H). LCMS (ES⁺) RT 1.34 min, 540.0 (M+H)⁺. [α]+39.7°.

Example 2—Analytical Size Exclusion Chromatography (SEC) of TNFα/TNFR1/Compound Complexes Size exclusion chromatography was used to determine the number of TNFR1 receptors bound to TNFα in the absence or presence of different compounds. Compound (2) was tested under the conditions described in protocol 1 below. Compound (5) was tested as described in protocol 2.

Protocol 1

Compound (2) was added to 300 μM of fused TNFα trimer at a final concentration range from 90 μM to 690 μM compound with the DMSO concentration held constant at 1.0%. The sample of TNFα and compound were incubated overnight at a temperature of 4° C.

Receptor at a final concentration of 240 µM (3.2 fold excess over trimers) was added to 75 µM compound-trimer complex prepared as described above. The final concentration of DMSO was 0.25%. The mixture was incubated for 1 hour at 22° C.

Conditions for analytical size exclusion using HPLC were as follows: injection volume: 50 µl; TSK G3000SW L×I.D. 30 cm×7.5 mm column, 10 µm particle size; buffer of 10 mM HEPES, pH 7.5, 150 mM NaCl. For the proteins, a single polypeptide chain of trimeric human TNFα composed of human TNFα residues V77-L233 followed by two additional repeats of human TNFα residues D86-L233 linked together by Ser-Gly-Ser (sequence based on UniProt P10375). Human TNFR1 (V43-N184)(N54D, C182S) was based on sequence P19438 (UniProt).

Results are presented in FIG. 5. In the Figure, the numbers 1-3 refer to the number of receptors bound to TNFα trimers. As shown in this Figure, addition of increasing concentrations of compound (2) resulted in the number of receptors bound reducing from three on average per trimer to two on average per trimer. In particular, at low concentrations of the compound (90 µM), a peak is observed showing three receptors binding per trimer (with a slight shoulder for two receptors binding per trimer). At an excess concentration of the compound (690 µM) the predominant peak corresponds to two receptors binding per trimer, with a slight shoulder corresponding to a peak for three receptors binding per trimer. Therefore, at this concentration of the compound the majority of trimer compound complexes bind two receptors.

In a separate experiment to observe the expected migration of one, two and three receptors bound to TNFα, a range of TNFR1 concentrations (1.2, 2.2, 3.2 and 5 fold excess relative to the concentration of TNFα trimer) were added to TNFα. Results are presented in FIG. 6. As shown in this Figure, increasing the concentration of receptors increases the molecular weight of the complex (shifts left) suggesting that the number of receptors binding per trimer shifts from one, through to three. Three receptors maximally occupies the TNFα trimer since increasing the TNFR1 concentration further has no effect.

Protocol 2

Compound (5) was added to 20 µM of TNFα trimer at a final concentration of 200 µM (ratio of 1:10 trimers:compound) with DMSO concentration held constant at 2.0%. The sample of TNFα and compound were incubated overnight at a temperature of 4° C. Receptors at a final concentration of 35 µM were added to 10 µM trimer-compound complex (3.5 fold excess of receptors over the trimer-compound complex). The final concentration of DMSO was 1.0%. The mixture was incubated for 1 hour at 22° C.

The conditions for analytical size exclusion using HPLC were as follows: injection volume: 50 µl; Superdex 200HR 10/300, L×I.D. 30 cm×10 mm column, 13-15 µm particle size; and a buffer of 10 mM HEPES, pH 7.5, 150 mM NaCl.

The TNFα was a single polypeptide chain of trimeric human TNFα composed of human TNFα residues V77-L233 followed by two additional repeats of human TNFα residues D86-L233 linked together by Ser-Gly-Ser (sequences are based on UniProt P10375). Human TNFR1 was (V43-N184)(N54D, C182S) based on sequence UniProt P19438.

To establish markers for the expected migration of one, two and three receptors bound to TNFα, point mutants of human TNFα that disrupt interactions at one, two and three receptor binding sites were added to 3.5× receptors (a 3.5 excess of receptors to trimers) in buffer containing the same final concentration of 1.0% DMSO.

FIG. 7 shows an overlay of the compound (5) trace with the control trace showing TNFα mutated to bind 1, 2 and 3 receptors. As compared to compound (2), the peak containing compound (5) has moved closer to 1 receptor bound.

Example 3—Crystallography Showing the Ternary Complex of Murine TNFα-TNFR1-Compound (1)

The soluble form of mouse TNFα (VC 6535, UniProt P06804) was expressed as a fusion protein in *E. coli* and has the final sequence:

(SEQ ID NO: 1)
DKPVAHVVANHQVEEQLEWLSQRANALLANGMDLKDNQLVVPADGLYLVY

SQVLFKGQGCPDYVLLTHTVSRFAISYQEKVNLLSAVKSPCPKDTPEGAE

LKPWYEPIYLGGVFQLEKGDQLSAEVNLPKYLDFAESGQVYFGVIAL.

Cells were pre-cultured at 37° C. in rich media, induced with the addition of 0.1% arabinose and allowed to express overnight at 25° C. in vector pEMB54. This vector introduces a cleavable N-terminal His$_6$Smt-tag. The cells were lysed and purified by Ni-NTA chelate chromatography. The fusion protein was eluted with buffer containing imidazole and cleaved by the addition of protease. The final cleaved TNFα protein was purified by a subtractive Ni chelate chromatography step to remove the fusion tag and further purified by size exclusion chromatography to remove the remaining impurities. The final TNFα product was concentrated to 20.5 mg/ml and flash frozen in liquid nitrogen.

The extracellular domain of human TNFR1 (VC 5602, UniProt P19438) was expressed as a secreted protein in baculovirus infected insect cells and has the final sequence:

(SEQ ID NO: 2)
GSVCPQGKYIHPQDNSICCTKCHKGTYLYNDCPGPGQDTDCRECESGSFT

ASENHLRHCLSCSKCRKEMGQVEISSCTVDRDTVCGCRKNQYRHYWSENL

FQCFNCSLCLNGTVHLSCQEKQNTVCTCHAGFFLRENECVSSSN

The fusion protein plasmid was cloned into the pEMB50 expression vector, which encodes a cleavable N-terminal secretion signal and His-tagged fusion protein. Virus was generated using the baculovirus expression system. Infected insect cells secreted the fusion protein into the media. The fusion protein was purified by Ni-NTA chelate chromatography and eluted from the Ni column using an imidazole gradient. The eluted protein was cleaved with protease to release the N-terminal His-fusion tag. The cleaved TNFR1 was subsequently purified by a subtractive Ni chelate chromatography step and further purified by size exclusion chromatography. The final TNFR product was concentrated to 8.8 mg/ml and flash frozen in liquid nitrogen.

Purified mouse TNFα (20.5 mg/ml, VC 6535) was incubated with compound (1) (100 mM in DMSO) in 6 molar excess at 37° C. for 3 hours followed by overnight incubation at 4° C. The following day, human TNFR1 (8.8 mg/ml, VC 5602) was added for a final molar ratio of 3 TNFα monomers (equivalent to 1 trimer):3 TNFR1 receptor. The ternary complex (cytokine, ligand, receptor) was incubated for 1 hour prior to loading on Superdex 200 size exclusion column (23 ml) that was pre-equilibrated with 10 mM HEPES pH 7.5, 150 mM NaCl. The final purified ternary complex was concentrated to 18.5 mg/ml and immediately used in crystallization trials.

The ternary complex was crystallized by sitting drop vapor diffusion by mixing 0.5 µl of complex with 0.5 µl of 800 mM sodium potassium tartrate, 0.5% PEG5000 MME, 100 mM Tris pH 8.5 over 100 µl of the same crystallization solution. Crystals were harvested for data collection approximately 2 months after initial set up. They were briefly soaked in paraffin oil and frozen directly in liquid nitrogen for data collection on Aug. 17, 2012 at Argonne Photon Source, beamline 21-IDF.

The structure of the mouse TNFα (VC 6535) and human TNFR (VC 5602) complex with compound (1) was solved by molecular replacement using Phaser with input models based upon a complexed human TNFα structure. Data were integrated in XDS and scaled using SCALA. Initial structure determination and refinement used data to 3.15 Å resolution from a single crystal. Iterative manual model building using Coot (Emsley, P. and Cowtan, K. 2004. Coot: model-building tools for molecular graphics. Acta Crystallogr. D Biol. Crystallogr. December; 60(Pt 12 Pt 1):2126-32. PMID: 15572765) and in Refmac (Murshudov, G. N., Vagin, A. A., and Dodson, E. J. 1997. Refinement of macromolecular structures by the maximum-likelihood method. May 1; 53(Pt3):240-55. PMID: 15299926) continued until R and $R_{free}$ reached R=0.222, $R_{free}$=0.272. Model quality was validated using Coot and MolProbity (Lovell, S. C., Davis, I. W., Arendall W. B., de Bakker, P. I., Word, J. M., Prisant, M. G., Richardson, J. S., and Richardson, D. C. 2003. Structure validation by Dalpha geometry: phi, psi and Cbeta deviation. Proteins. February 15; 50(3):437-50. PMID: 12557186). Final data processing and refinement statistics are listed in Table 1.

TABLE 1

Data collection and refinement statistics.

| Data collection | Dataset 1 |
| --- | --- |
| Crystal ID | 234879c07 |
| Beamline | APS 21-IDF |
| Collection date | Aug. 17, 2012 |
| Oscillation width (°) | 1.0 |
| Frames | 60 |
| Exposure (sec) | 3 |
| Distance (mm) | 300 |
| Wavelength (Å) | 0.97872 |
| Data processing | (outer shell) |
| Space Group | $P\,4_1\,2_1\,2$ |
| Unit cell (Å, °) | a = b = 133.577, c = 141.445; $\alpha = \beta = \gamma = 90$ |
| Resolution (Å) | 3.15 |
| I/σ | 8.3 (1.8) |
| Completeness (%) | 99.9 (100) |
| Rpim | 0.095 (0.45) |
| $R_{merge}$ (%) | 0.19 (0.90) |
| Reflections (unique) | 18,167 (1,314) |
| Multiplicity | 4.8 (5.0) |
| Refinement statistics | |
| $R_{work}/R_{free}$ overall | 22.2/27.2 |
| RMSD bonds (Å) | 0.011 |
| RMSD angles (°) | 1.222 |
| Ramachandran outliers (%) | 0.9 |
| Ramachandran favored (%) | 95.9 |
| Molprobity score | 1.91; 100th percentile* (N = 2048, 3.15 Å ± 0.25 Å) |
| Peer Reviewed by: | David Fox |

*100th percentile is the best among structures of comparable resolution; 0th percentile is the worst.

The crystal structures, as presented in FIG. 8A-D, show two receptors binding per trimer-compound complex.

Example 4—TNFα—TNFR1 TR-FRET

A homogenous Time Resolved Fluorescent Resonance Energy Transfer (TR-FRET) assay was developed to measure compound mediated reduction in TNF Receptor 1 (TNFR1 extracellular domain (ECD)) binding to a fused TNFα trimer.

Terbium labelled Streptavidin, in complex with a biotinylated fused TNFα trimer, formed the donor portion of the FRET pair. Alexa Fluor 488 (AF488) conjugated TNFR1 (ECD) was used as the FRET acceptor.

TABLE 2

Protein constructs and labels for FRET assays

| Protein Construct | Label |
| --- | --- |
| TNFR1(ECD)-6xLysine -Human single chain Fc | Amine reactive Alexa Fluor 488 5-TFP (Life technologies, A30005) |
| TNFα (fused trimer) - AVI Tag | Biotin molecule on AVI Tag (Avidity, Biotin-protein ligase, EC 6.3.4.15) |
| Streptavidin | LanthaScreen Amine Reactive Terbium Chelate (Life Technologies, PV3581) |

Each of the labelled proteins was diluted to a final assay concentration of 7.5 nM (a 1:1 concentration ratio of TNF monomers:receptors) in a buffer solution (20 mM Tris, 150 mM NaCl, 0.05% Tween 20, pH 7.2). Compounds were tested in a 10 point titration with three fold dilution. The maximum compound concentration in the final assay was 25 µM. The final DMSO concentration of the assay was 5% by volume.

After incubating for twenty hours the plate was read using an LJL Analyst plate reader. The samples were excited at 330 nm and fluorescence readings were taken at 495 nm and 520 nm, the emission wavelengths of the Terbium donor and AF488 acceptor, respectively. A FRET ratio was calculated by dividing the acceptor counts by the donor counts and multiplying by 10,000.

In the absence of an interfering molecule TNFR1 will form a complex with the fused TNFα trimer generating a FRET signal. An interfering molecule will prevent TNFR1 from binding and subsequently will inhibit the FRET signal.

The inhibition of FRET may be either complete or partial, whereby there is a reduction in bound TNFR1 (ECD) indicating a reduction in TNFα-TNFR1 (ECD) stoichiometry. Complete inhibition as by an antibody is 100%.

Figure 9:
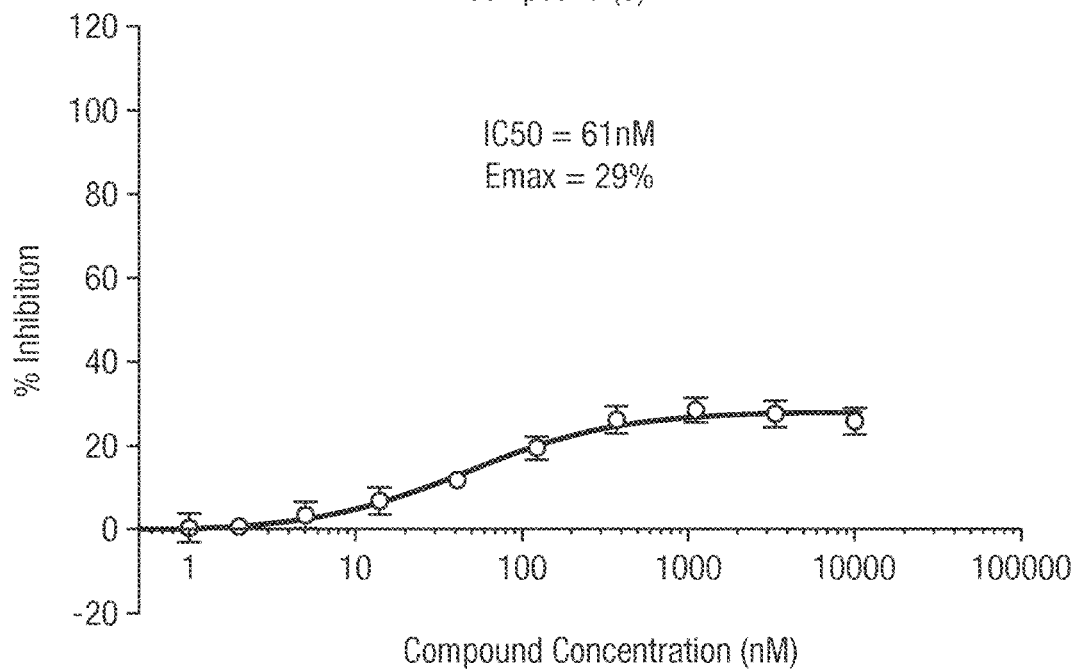
FIG. 9 shows results of FRET experiments with increasing concentrations of compound (3). Complete inhibition as would be observed with a blocking antibody would result in no receptor binding to TNFα i.e. complete inhibition of a FRET signal. In this instance the FRET signal is partially inhibited. At the highest concentrations of the compound, maximal inhibition is 29%, suggesting that one out of the three receptors is inhibited from binding to the TNF trimer.
Figure 10:
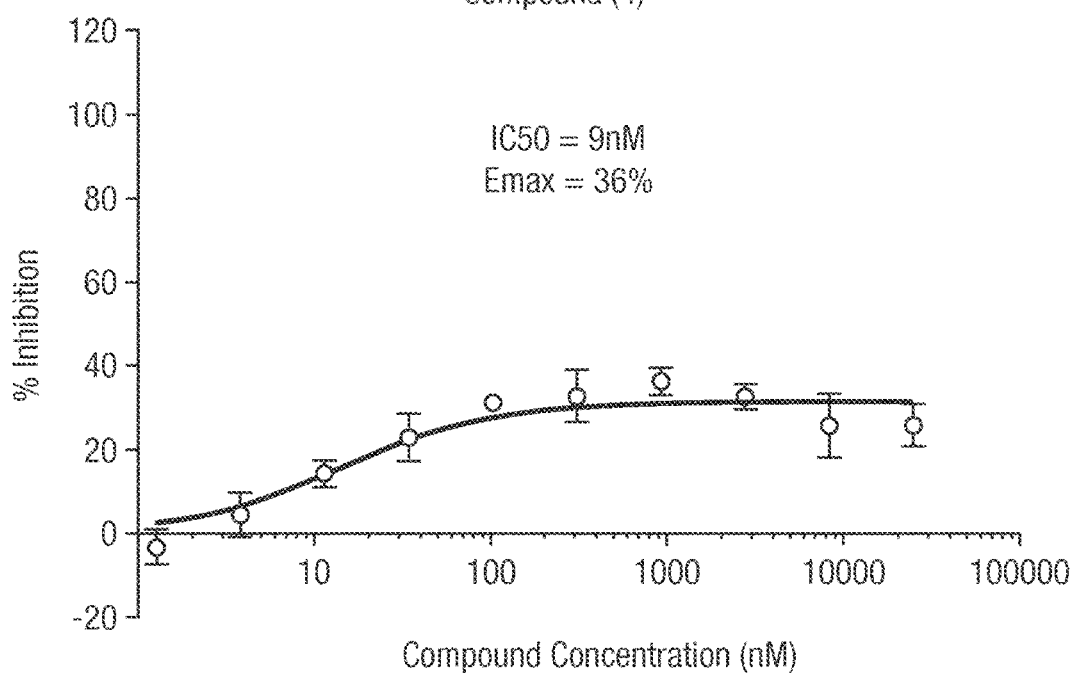
FIG. 10 shows results of FRET experiments with increasing concentrations of compound (4). Again, the FRET signal is partially inhibited. At the highest concentrations of the compound, maximal inhibition is 36%. Similar to the observation described in FIG. 9, this suggests that one out of the three receptors is inhibited from binding to the TNF trimer.

FIGS. 9 and 10 represent a partial inhibition observed with compound (3) and compound (4). At the highest concentration of the compound the maximal inhibition is 29% and 36%, respectively. This corresponds to an average inhibition of one out of a possible three receptors binding (expected 33%)

Example 5—Analysis of TNF Receptor Binding Stoichiometry by Ion-Mobility Mass Spectrometry Human TNFα was desalted and buffer exchanged into 20 mM ammonium acetate, pH 7.4 prior to use. A combination of zeba spin columns (Thermo-Fisher, 7 kDa MWCO) followed by micro-dialysis (Thermo slide-a-lyzer mini dialysis units, 10 kDa MWCO) ensured that the protein was fully desalted and produced well-resolved signals by native mass spectrometry. TNFα (20 µM) was added 1:1 (v:v) with a small molecule TNFα inhibitor (compound (3)), 200 µM, 2% DMSO. Compound was diluted from a 10 mM DMSO stock using 20 mM ammonium acetate, pH 7.4). A DMSO-only control was also prepared where TNFα (20 μM) was added 1:1 (v:v) with buffer (20 mM, ammonium acetate, pH 7.4, 2% DMSO). Both solutions were incubated at room temperature overnight, after which the small molecule-containing sample was analysed by non-covalent time-of-flight mass spectrometry (Waters LCT Premier, equipped with Advion TriVersa NanoMate souce) for confirmation that the TNFα was fully bound.

Human TNFR1 (residues 41-184, C182S, de-glycosylated) was prepared for native MS analysis by buffer exchanging into 20 mM ammonium acetate, pH 7.4 using a zeba spin column (Thermo-Fisher, 7 kDa MWCO). Receptor was added 1:1 (v:v) to aliquots of the TNFα samples prepared previously, to give three samples per experiment containing 5, 10 and 23 μM TNFR (final TNFα concentration in each sample was 5 μM). Samples were incubated for 2 hours and analysed by ion-mobility mass spectrometry (Waters Synapt G2 Q-TOF mass spectrometer, equipped with Advion TriVersa NanoMate souce).

Receptor stoichiometry can be uniquely determined by mass spectrometry due to the significant mass differences obtained when 1, 2 or 3 receptors bind to TNFα. Problems are encountered however due to overlapping charge states on the mass-to-charge (m/z) scale used, e.g. the same m/z value of 2000 would be obtained from an analyte (MW 20,000 Da) with 20 charges, as an analyte (MW 32,000) with 16 charges. Ion mobility mass spectrometry is therefore required for these experiments due to the extra degree of separation obtained by measurement of both 'drift time' and mass-to-charge. The drift time of an analyte is dependent on its mass, charge, and conformation, and is measured as the length of time taken for each analyte to traverse a gas-filled mobility cell inside the spectrometer. The resulting two-dimensional plots of m/z versus drift time allow unambiguous assignment of receptor stoichiometry.

Figure 11:
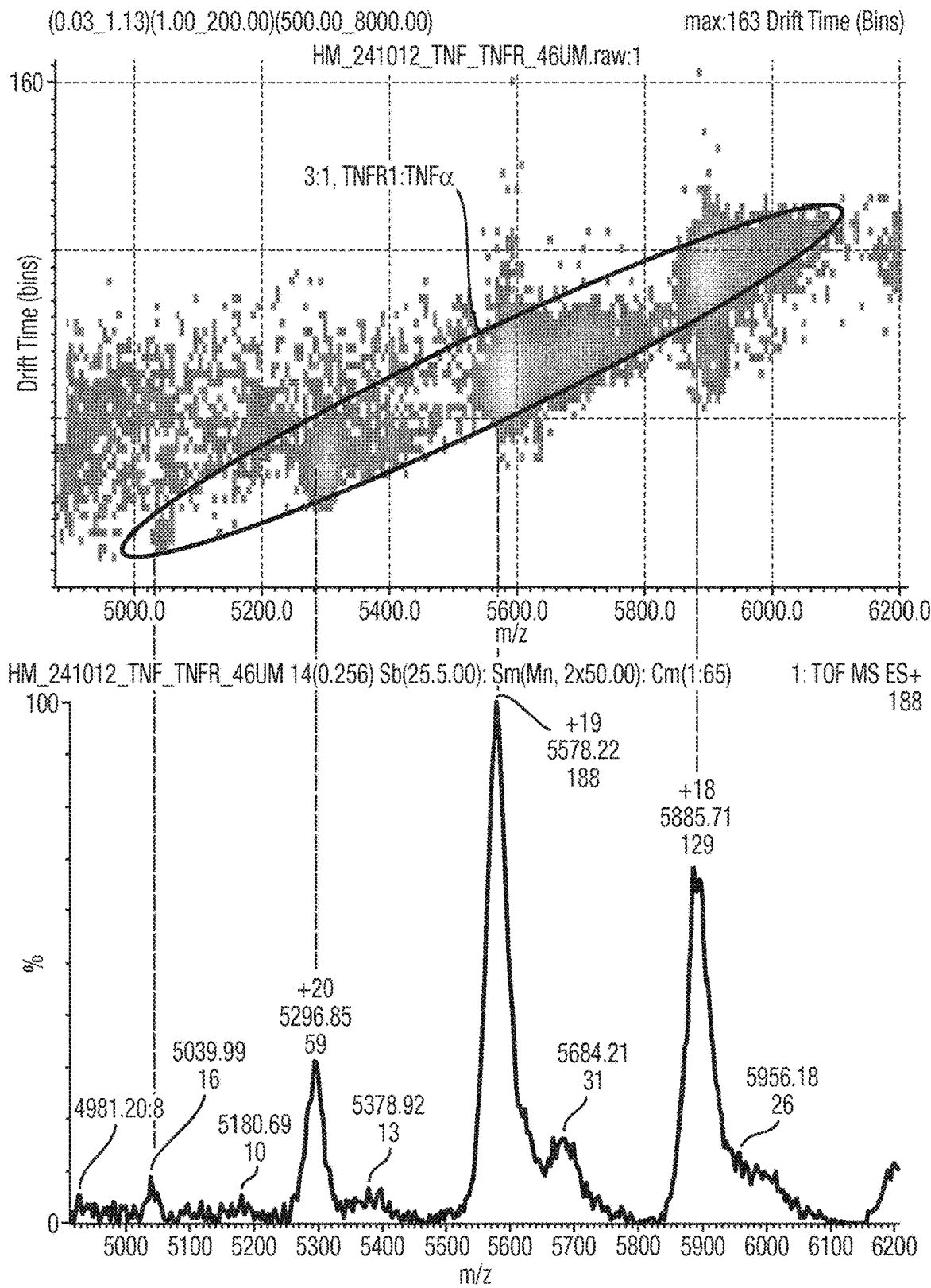
FIG. 11 shows an analysis of receptor binding stoichiometry by ion-mobility mass spectrometry. In the control (comprising TNFα and an excess of TNFR1), three receptors are shown to bind on average per trimer compound-complex. In contrast, in the presence of compound (3) the receptor stoichiometry is reduced and predominantly two receptors bind per trimer-compound complex.
Figure 11:
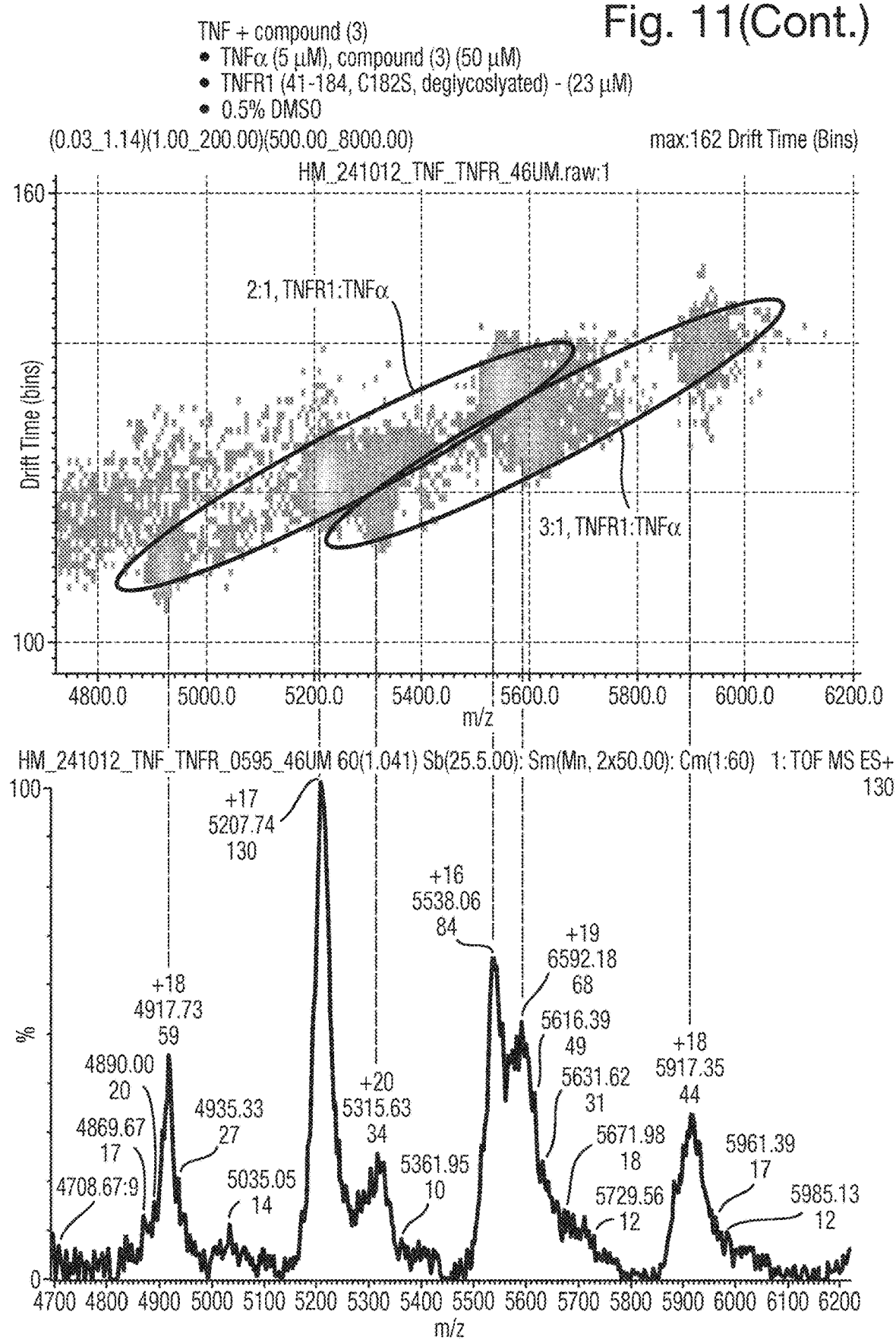

In the control experiment, when the molar excess of added TNFR was greater than three-times the concentration of TNFα, three receptors were observed binding per TNFα trimer. In the presence of a small molecule TNFα inhibitor such as compound (3), the receptor stoichiometry was reduced and predominantly two receptors were bound per TNFα trimer (see FIG. 11).

Example 6—Mass Spectrometry Analysis Measuring the Effects of Compound (3) on TNFR1 Affinity for TNFα

Compound Stock:

2 μl of 10 mM DMSO stock, plus 2 μl DMSO were added to 96 μl of 20 mM ammonium acetate buffer to give 100 μl 200 μM compound (3), 4% DMSO.

Protein Stocks:

TNF was desalted using 2× Zeba column followed by dialysis into 20 mM ammonium acetate pH 7.4. TNFR was desalted using 2× zeba column followed by dialysis into 20 mM ammonium acetate pH 7.4. An A280 measurement was taken to confirm the final concentration of protein samples.

Compounds were added 1:1 (v:v) to TNF (40 μM) and incubated overnight at room temperature. (Final DMSO concentration=2%)

A DMSO-only control sample was also prepared.

For each sample, 5 μL TNF plus compound or TNF plus DMSO-only was added to 5 μL TNFR at each concentration specified. Final [TNF] was 5 μM.

Samples were incubated with TNFR for 2 hours prior to analysis.

Solutions containing 5000 nM hTNFα and 5000 nM hTNFα in the presence of compound (3) were titrated with hTNFR1 (extracellular domain comprising residues 41 to 184) in the range of concentrations of 1000, 2000, 4000, 6000, 8000, 10000 and 23000 nM.

Ion Mobility Mass Spectral analysis was performed on Advion Nanomate—Waters Synapt G2 instrument. The following instrument parameters were utilised.

Cone=50V
Source temp=20 C
Trap/transfer collision energy=off
Trap gas flow=0.4 mL/min
Helium cell=180 mL/min,
IMS (N2)=90 mL/min
Trap DC bias=40V
Mobility trapping manual release—not enabled
IMS wave delay=450 us
IMS wave velocity=750 m/s
IMS wave height 40 V
Backing=6.21 mbar
trap 2.05e-2 mbar
IMS 3.47 mbar
TOF 1.2e-6 mbar
Quad profile:
4000, 5000, 6000 (dwell 30, ramp 30)
Range 500-8000

Data was analysed by extracting mass spectra for each species within driftscope software. The resulting spectra were smoothed (50/5) and peak heights summed over all charge states.

The ion counts of peaks corresponding to species TNF (no receptor bound), TNF+1R (one receptor bound), TNF+2R (two receptors bound) and TNF+3R (three receptors bound) were measured. Normalised ion counts were calculated as the fraction of ions of each species divided by the total amount of ions counted. These values were used as equivalent to molar fraction of each species in equilibrium. Data from the two experiments are summarised in the tables below:

TABLE 3

| Initial Concentration | | Normalised Ion Count | | | |
|---|---|---|---|---|---|
| hTNFα Trimer [nM] | hTNFR1 [nM] | TNF | TNF + 1R | TNF + 2R | TNF + 3R |
| 5000 | 1000 | 0.973 | 0.027 | 0.000 | 0.000 |
| 5000 | 2000 | 0.767 | 0.233 | 0.000 | 0.000 |
| 5000 | 4000 | 0.421 | 0.525 | 0.054 | 0.000 |
| 5000 | 6000 | 0.121 | 0.547 | 0.332 | 0.000 |
| 5000 | 8000 | 0.000 | 0.331 | 0.669 | 0.000 |
| 5000 | 10000 | 0.000 | 0.000 | 0.720 | 0.280 |
| 5000 | 23000 | 0.000 | 0.000 | 0.000 | 1.000 |

TABLE 4

| Initial Concentration | | Normalised Ion Count | | | |
|---|---|---|---|---|---|
| hTNFα Trimer [nM] + compound (3) | hTNFR1 [nM] | TNF | TNF + 1R | TNF + 2R | TNF + 3R |
| 5000 | 1000 | 0.869 | 0.131 | 0.000 | 0.000 |
| 5000 | 2000 | 0.789 | 0.211 | 0.000 | 0.000 |
| 5000 | 4000 | 0.396 | 0.558 | 0.046 | 0.000 |
| 5000 | 6000 | 0.113 | 0.665 | 0.222 | 0.000 |
| 5000 | 8000 | 0.034 | 0.490 | 0.476 | 0.000 |

TABLE 4-continued

| Initial Concentration | | | | | |
|---|---|---|---|---|---|
| hTNFα Trimer [nM] + compound (3) | hTNFR1 [nM] | Normalised Ion Count | | | |
| | | TNF | TNF + 1R | TNF + 2R | TNF + 3R |
| 5000 | 10000 | 0.000 | 0.050 | 0.950 | 0.000 |
| 5000 | 23000 | 0.000 | 0.000 | 0.713 | 0.287 |

In order to derive equilibrium constants from these data, the system in equilibrium was represented by the transformations:

$$\text{Error}(K1, K2, K3) = \sum_{T0,Rmin}^{T0,Rmax} [(f_{TNF_{calc}} - f_{TNF_{obs}})^2 + (f_{TNF+1R_{calc}} - f_{TNF+1R_{obs}})^2 + (f_{TNF+2R_{calc}} - f_{TNF+2R_{obs}})^2 + (f_{TNF+3R_{calc}} - f_{TNF+3R_{obs}})^2]_{T0,R}^{1/2}$$

To calculate the set of dissociation constants K1, K2 and K3 in best agreement with native mass spectrometry data, values of K1, K2, K3 that produce molar fractions of the species TNF, TNF+1R, TNF+2R and TNF+3R closest to the measured molar fractions of those species were obtained by minimisation of the function:

$$TNF + R \overset{K1}{\leftrightarrow} TNF + 1R$$
$$TNF + 1R + R \overset{K2}{\leftrightarrow} TNF + 2R$$
$$TNF + 2R + R \overset{K3}{\leftrightarrow} TNF + 3R$$

where T0 represents the initial amount of TNF and Rmin, R, Rmax represent the initial concentration of Receptor R assayed starting from Rmin and ending at Rmax. Fractions $f_{obs}$ are the molar fractions of species TNF, TNF+1R, TNF+2R and TNF+3R observed in equilibrium (ex. $f_{TNFobs}$) by native mass spectrometry measurements. $f_{calc}$ are the molar fractions for each species (ex. $f_{TNFcalc}$) calculated by solving the equilibrium equations using the BioNetGen BNGL modelling tool (Blinov, M. L., Faeder, J. R., Goldstein, B., and Hlavacek, W. S. (2004) BioNetGen: software for rule-based modeling of signal transduction based on the interactions of molecular domains. Bioinformatics 20, 3289-3291.) and taking as input the values of T0, R0 and K1, K2 and K3. The Error function was minimised using the brute force minimisation utility implemented within the SciPy/NumPy framework (http://docs.scipy.org/doc/numpy/index.html). The entire data processing analysis was implemented in the Python programming language (https://www.python.org/) calling BioNetGen routines when necessary.

After data analysis, three equilibrium constants (K1, K2 and K3) corresponding to the three receptor binding events were calculated for the mixtures of TNF and receptor with and without compound (3). Data were visualised by plotting on the "Y" axis the molar fractions of all species in equilibrium and on the "X" axis, the concentration of receptor added to a fixed initial concentration of TNF. Symbols represent the observed molar fractions of species measured in the native mass spectrometry experiment and traces correspond to the expected concentrations calculated from the equilibrium constants K1, K2 and K3. These graphs are presented in FIGS. 12 and 13.

TABLE 5

| Sample | K1 [nM] | K2 [nM] | K3 [nM] |
|---|---|---|---|
| TNF + Receptor | 0.01 | 0.02 | 0.22 |
| TNF + Receptor + compound (3) | 0.04 | 0.19 | 9612 |

Example 7—Compounds and Complexes of Ma et al (2014) and Silvian et al (2011) have Different Characteristics to Those of the Present Invention As described on page 12458 of Ma et al. (2014) JBC 289:12457-12466, C87 was discovered through virtual screening by attempting to find molecules which fit the space occupied by a 7 amino-acid peptide from loop2/domain2 of TNFR1 in its interaction with the external surface of TNFβ. The C87 compound from Ma et al. and the BIO08898 compound from Silvian et al. (2011) ACS Chemical Biology 6:636-647 were tested by the present inventors.

Summary of Findings

The Biacore observations described in Ma et al. for C87 could not be repeated.

No evidence of TNF specific inhibition in cells was observed.

Additionally C87 was not observed to bind by mass spectrometry, which is sensitive to millimolar affinities.

Extensive crystallography trials only produced apo-TNF (TNF without compound).

In the fluorescence polarisation (FP) assay, C87 showed no significant inhibition above the interference level of the compound with the fluorescent read-out.

Thermofluor, which measures stabilisation of the thermal melting temperature of TNFα, did show a small stabilisation for C87.

In summary, no evidence was found that C87 binds in the centre of the trimer. The overwhelming majority of the data suggested no direct interaction with TNFα. BIO08898 was also found not to bind to TNFα.

Cells—TNF Induced HEK NFKB Reporter Gene Assay

C87 was preincubated with TNFα for 1 hour prior to the addition to HEK-293 cells stably transfected with SEAP under the control of NFκB. An appropriate counter-screen was also tested in order to detect non-TNF related (off target) activity. The assay was incubated overnight before inhibition was measured compared to 100% blocking by a control compound. The maximum C87 concentration was 10,000 nM, with a 3-fold serial dilution.

No inhibitory effect could be detected that could not be attributed to off-target activity.

Biacore

TNF was immobilised using an avi-tag linker and C87 was passed over the chip. In one experiment, a dose response of C87 from a highest concentration of 10 μM was performed. No binding was observed.

In a second experiment, the flow rate of C87 passing over the chip was reduced. A small shift was observed but overall binding was negligible.

The binding of C87 to TNF described in Ma et al was likely to be super-stoichiometric based on the RU value on the Y-axis. At standard TNF density on the chip this value was in the region of thirty times higher than expected for simple 1:1 binding.

In another experiment, BIO08898 was tested against the immobilised soluble form of CD40L and the soluble form of TNFα by SPR on a Biacore 4000 machine. A geomean IC50 of 17 µM was determined for binding against CD40L whereas no binding was detected at a concentration of up to 100 µM for TNFα in this assay.

Mass Spectrometry

There was no evidence of C87 binding to human TNFα (20 µM) at a concentration of 400 µM. A species of lower molecular weight (~473 Da appears to bind at less than 5% occupancy). C87 has a molecular weight of 503 Da. Based on the occupancy at a concentration of 400 µM, an affinity of the low molecular weight species in excess of 1 mM is predicted.

Crystallography

Overall a large effort was put into crystallising C87 with TNFα, including testing conditions that routinely work with compounds described in the present application. This comprised setting up a large number of crystallization trials at different ligand concentrations, different protein concentrations, and different soaking times. A few crystals were observed that, on analysis, proved to be salt or TNF with no compound.

Fluorescent Polarization (FP)

C87 was preincubated with TNFα for 1 hour prior to assay against the fluorescent compound (probe). Competition with the fluorescent compound either directly (binding at the same site) or indirectly (disrupting TNF) is detected by a reduction in FP.

Extrapolation of the inhibition curve produced an IC50 of about 100 µM. Fluorescence quenching was, however, observed at the highest concentrations of inhibitor which, when subtracted, resulted in negligible inhibition of C87 in this assay.

Thermofluor

Thermofluor measures the change of melting temperature (Tm) of TNFα due to compound either stabilising or disrupting the protein. A stabilization effect of 3.8° C. was observed at a concentration of 500 µM C87, suggesting the possibility of weak binding, which may not be specific.

```
Sequence listing
                                           SEQ ID NO: 1
DKPVAHVVANHQVEEQLEWLSQRANALLANGMDLKDNQLVVPADGLYLVY

SQVLFKGQGCPDYVLLTHTVSRFAISYQEKVNLLSAVKSPCPKDTPEGAE

LKPWYEPIYLGGVFQLEKGDQLSAEVNLPKYLDFAESGQVYFGVIAL

SEQ ID NO: 2
GSVCPQGKYIHPQDNSICCTKCHKGTYLYNDCPGPGQDTDCRECESGSFT

ASENHLRHCLSCSKCRKEMGQVEISSCTVDRDTVCGCRKNQYRHYWSENL

FQCFNCSLCLNGTVHLSCQEKQNTVCTCHAGFFLRENECVSSSN (HCVR of 1974)
                                           SEQ ID NO: 3
DVQLVESGGGLVQPGRSLKLSCAASGFTFSAYYMAWVRQAPTKGLEWVAS

INYDGANTFYRDSVKGRFTVSRDNARSSLYLQMDSLRSEDTATYYCTTEA

YGYNSNWFGYWGQGTLVTVSS (LCVR of 1974)
                                           SEQ ID NO: 4
DIQMTQSPASLPASPEEIVTITCQASQDIGNWLSWYQQKPGKSPQLLIYG

ATSLADGVPSRFSASRSGTQYSLKISRLQVEDFGIFYCLQGQSTPYTFGA

GTKLELK (1974 HC mIgG1 full)
                                           SEQ ID NO: 5
DVQLVESGGGLVQPGRSLKLSCAASGFTFSAYYMAWVRQAPTKGLEWVAS

INYDGANTFYRDSVKGRFTVSRDNARSSLYLQMDSLRSEDTATYYCTTEA

YGYNSNWFGYWGQGTLVTVSSAKTTPPSVYPLAPGSAAQTNSMVTLGCLV

KGYFPEPVTVTWNSGSLSSGVHTFPAVLQSDLYTLSSSVTVPSSTWPSET

VTCNVAHPASSTKVDKKIVPRDCGCKPCICTVPEVSSVFIFPPKPKDVLT

ITLTPKVTCVVVDISKDDPEVQFSWFVDDVEVHTAQTQPREEQFNSTFRS

VSELPIMHQDWLNGKEFKCRVNSAAFPAPIEKTISKTKGRPKAPQVYTIP

PPKEQMAKDKVSLTCMITDFFPEDITVEWQWNGQPAENYKNTQPIMDTDG

SYFVYSKLNVQKSNWEAGNTFTCSVLHEGLHNHHTEKSLSHSPGK (1974 LC kappa full)
                                           SEQ ID NO: 6
DIQMTQSPASLPASPEEIVTITCQASQDIGNWLSWYQQKPGKSPQLLIYG

ATSLADGVPSRFSASRSGTQYSLKISRLQVEDFGIFYCLQGQSTPYTFGA

GTKLELKRTDAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC (HCVR of 1979)
                                           SEQ ID NO: 7
EVHLVESGPGLVKPSQSLSLTCSVTGYSITNSYWDWIRKFPGNKMEWMGY

INYSGSTGYNPSLKSRISISRDTSNNQFFLQLNSITTEDTATYYCARGTY

GYNAYHFDYWGRGVMVTVSS (LCVR of 1979)
                                           SEQ ID NO: 8
DIQMTQSPASLSASLEEIVTITCQASQDIGNWLSWYQQKPGKSPHLLIYG

TTSLADGVPSRFSGSRSGTQYSLKISGLQVADIGIYVCLQAYSTPFTFGS

GTKLEIK (1979 HC mIgG1 full)
                                           SEQ ID NO: 9
EVHLVESGPGLVKPSQSLSLTCSVTGYSITNSYWDWIRKFPGNKMEWMGY

INYSGSTGYNPSLKSRISISRDTSNNQFFLQLNSITTEDTATYYCARGTY

GYNAYHFDYWGRGVMVTVSSAKTTPPSVYPLAPGSAAQTNSMVTLGCLVK

GYFPEPVTVTWNSGSLSSGVHTFPAVLQSDLYTLSSSVTVPSSTWPSETV

TCNVAHPASSTKVDKKIVPRDCGCKPCICTVPEVSSVFIFPPKPKDVLTI

TLTPKVTCVVVDISKDDPEVQFSWFVDDVEVHTAQTQPREEQFNSTFRSV

SELPIMHQDWLNGKEFKCRVNSAAFPAPIEKTISKTKGRPKAPQVYTIPP

PKEQMAKDKVSLTCMITDFFPEDITVEWQWNGQPAENYKNTQPIMDTDGS

YFVYSKLNVQKSNWEAGNTFTCSVLHEGLHNHHTEKSLSHSPGK (1979 LC Kappa full)
                                           SEQ ID NO: 10
DIQMTQSPASLSASLEEIVTITCQASQDIGNWLSWYQQKPGKSPHLLIYG

TTSLADGVPSRFSGSRSGTQYSLKISGLQVADIGIYVCLQAYSTPFTFGS

GTKLEIKRTDAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC
```

The invention claimed is:

1. A method of identifying a compound that binds to trimeric TNFα and modulates signalling of the trimeric TNFα through a TNF receptor, the method comprising determining the average number of receptors bound per trimer-compound complex in comparison with a control, wherein the average number of receptors bound per trimer-compound complex is determined by:
   (i) ion mobility mass spectrometry;
   (ii) size exclusion chromatography;
   (iii) Förster Resonance Energy Transfer;
   (iv) crystallography; or
   (v) a combination thereof, wherein:
   (a) the control comprises trimeric TNFα and TNF receptors in the absence of the compound, wherein a decrease in the average number of receptors bound per trimer-compound complex in comparison with the control identifies that the compound modulates signalling through the receptor; or
   (b) the control comprises trimeric TNFα and TNF receptors, and a compound which is known to modulate signalling of the trimers through the receptors and an equivalent average number of receptors bound per trimer-compound complex in comparison with the control, or decrease in the average number of receptors bound per trimer-compound complex in comparison with the control, identifies that the compound modulates signalling through the receptor.

2. The method of claim 1, wherein the average number of receptors bound per trimer-compound complex is determined at a molar ratio of between 3:1 and 10:1 (receptors:trimers).

3. The method of claim 1, wherein a compound is identified as modulating signalling of the trimeric TNFα through the receptor if an average of less than three receptors are determined to be bound per trimer-compound complex.

4. The method of claim 3, wherein a compound is identified as modulating signalling of the trimeric TNFα through the receptor if an average of two receptors are determined to be bound per trimer-compound complex.

5. The method of claim 3, wherein a compound is identified as modulating signalling of the trimeric TNFα through the receptor if an average of one receptor is determined to be bound per trimer-compound complex.

* * * * *